United States Patent
Bullock et al.

(10) Patent No.: US 11,633,589 B2
(45) Date of Patent: Apr. 25, 2023

(54) BIPHASIC INJECTABLE ELECTRODE

(71) Applicant: QV Bioelectronics Ltd., Nether Alderley (GB)

(72) Inventors: Christopher John Bullock, Nether Alderley (GB); Richard Zhiming Fu, Nether Alderley (GB); Nimrah Munir, Nether Alderley (GB)

(73) Assignee: QV Bioelectronics Ltd., Nether Alderley (GB)

( * ) Notice: Subject to any disclaimer, the term of this patent is extended or adjusted under 35 U.S.C. 154(b) by 0 days.

(21) Appl. No.: 17/653,598

(22) Filed: Mar. 4, 2022

(65) Prior Publication Data

US 2022/0280779 A1  Sep. 8, 2022

(30) Foreign Application Priority Data

Mar. 5, 2021 (GB) .................... 2103132

(51) Int. Cl.
*A61N 1/05* (2006.01)
*A61N 1/36* (2006.01)
*A61N 1/04* (2006.01)

(52) U.S. Cl.
CPC ......... *A61N 1/0534* (2013.01); *A61N 1/0436* (2013.01); *A61N 1/36002* (2017.08)

(58) Field of Classification Search
CPC ............... A61N 1/0534; A61N 1/0436; A61N 1/36002
See application file for complete search history.

(56) References Cited

U.S. PATENT DOCUMENTS

| | | |
|---|---|---|
| 6,978,180 B2 | 12/2005 | Tadlock |
| 7,096,070 B1 | 8/2006 | Jenkins et al. |
| 8,032,231 B1 | 10/2011 | Gilson et al. |
| 8,718,778 B2 | 5/2014 | Bikson et al. |
| 9,155,889 B2 | 10/2015 | Hershey |
| 9,179,875 B2 | 11/2015 | Hua |

(Continued)

FOREIGN PATENT DOCUMENTS

| | | |
|---|---|---|
| WO | WO-2006108229 A1 | 10/2006 |
| WO | WO-2008087489 A8 | 11/2008 |

(Continued)

OTHER PUBLICATIONS

"United Kingdom Application GB2103132.3, Combined Search and Examination Report dated Jul. 20, 2021", (Jul. 20, 2021), 2 pgs.

(Continued)

*Primary Examiner* — Mallika D Fairchild

(74) *Attorney, Agent, or Firm* — Schwegman Lundberg & Woessner, P.A.

(57) ABSTRACT

This specification generally relates to a biphasic injectable electrode which comprises a plurality of solid particles and a transporter phase, wherein both the solid particles and the transporter phase comprise poly(3,4-ethylenedioxythiophene)polystyrene sulfonate. The biphasic injectable electrode, in use in a surgical resection cavity in the brain includes inserting the biphasic injectable electrode into a surgical resection cavity in the brain with a tumor resection margin. A probe is inserted into the electrode and four counter electrodes are implanted in the surrounding brain tissue. A charge delivery device delivers charge to the probe via a wire both of which have also been implanted.

21 Claims, 4 Drawing Sheets

(56) References Cited

U.S. PATENT DOCUMENTS

| | | | |
|---|---|---|---|
| 2011/0087315 A1* | 4/2011 | Richardson-Burns | A61N 1/05 205/198 |
| 2011/0112394 A1 | 5/2011 | Mishelevich | |
| 2017/0266438 A1 | 9/2017 | Sano et al. | |
| 2019/0357847 A1 | 11/2019 | Franke et al. | |
| 2021/0038773 A1 | 2/2021 | Cui et al. | |

FOREIGN PATENT DOCUMENTS

| | | |
|---|---|---|
| WO | WO-2015017543 A2 | 2/2015 |
| WO | WO-2016179712 A1 | 11/2016 |
| WO | WO-2018005936 A1 | 1/2018 |
| WO | WO-2018072894 A1 | 4/2018 |
| WO | WO-2018111949 A1 | 6/2018 |
| WO | WO-2018119220 A1 | 6/2018 |
| WO | WO-2018227165 A1 | 12/2018 |
| WO | WO-2020018662 A1 | 1/2020 |
| WO | WO-2020047285 A1 | 3/2020 |
| WO | WO-2022184896 | 9/2022 |

OTHER PUBLICATIONS

"United Kingdom Application GB2103132.3, Examination Report dated Nov. 26, 2021", (Nov. 26, 2021), 1 pgs.

"United Kingdom Application GB2103132.3, Response to Combined Search and Examination Report dated Sep. 1, 2021", (Sep. 1, 2021), 4 pgs.

"United Kingdom Application GB2103132.3, Search Report dated Jul. 19, 2021", (Jul. 19, 2021), 1 pg.

Cogan, Stuart F., "Neural Stimulation and Recording Electrodes", Annu. Rev. Biomed. Eng. 2008, 10:275-309, (Apr. 22, 2008), 37 pgs.

Di Sebastiano, Andrea R., et al., "Preclinical outcomes of Intratumoral Modulation Therapy for glioblastoma", Scientific Reports | (2018) 8:7301, (May 8, 2018), 11 pgs.

Iredale, Erin, et al., "Optimization of multi-electrode implant configurations and programming for the delivery of non-ablative electric fields in intratumoral modulation therapy", Med. Phys. 47 (11), Nov. 2020, (Nov. 2020), 15 pgs.

Kirson, Eilon D., et al., "Alternating electric fields arrest cell proliferation in animal tumor models and human brain tumors", PNAS; 2007; 104(24):10152-7; doi:10.1073/pnas.0702916104, (Jun. 12, 2007), 10152-7.

Lu, Baoyang, et al., "Pure PEDOT:PSS hydrogels", Nature Communications | (2019) 10:1043 | https://doi.org/10.1038/s41467-019-09003-5 | www.nature.com/naturecommunications, (2019), 10.

Stupp, Roger, et al., "Effect of Tumor-Treating Fields Plus Maintenance Temozolomide vs Maintenance Temozolomide Alone on Survival in Patients With Glioblastoma", JAMA; 2017; 318(23):2306-16; doi: 10.1001/jama.2017.18718, (Dec. 19, 2017), 2306-16.

Toms, S. A., et al., "Increased compliance with tumor treating fields therapy is prognostic for improved survival in the treatment of glioblastoma: a subgroup analysis of the EF-14 phase III trial", Journal of Neuro-Oncology; 2019; 141(2):467-473; doi:10.1007/s11060-018-03057-z, (Dec. 1, 2018), 467-473.

Trevathan, James K., et al., "An Injectable Neural Stimulation Electrode Made from an In-Body Curing Polymer/Metal Composite", Adv. Healthcare Mater. 2019, 8, 1900892, (2019), 15.

Yeo, Yong Ho, et al., "Dual-crosslinked, self-healing and thermoresponsive methylcellulose/ chitosan oligomer copolymer hydrogels", Carbohydrate Polymers 258 (2021) 117705, (Jan. 30, 2021), 10.

"International Application No. PCT/EP2022/055558, Response to Written Opinion dated Jun. 14, 2022", (response filed Sep. 16, 2022), 4 pgs.

"International Application No. PCT/EP2022/055558, Written Opinion of the International Preliminary Examining Authority dated Oct. 10, 2022", (Oct. 10, 2022), 6 pgs.

"International Application No. PCT/EP2022/055558, International Search Report and Written Opinion dated Jun. 14, 2022", (Jun. 14, 2022), 12 pgs.

\* cited by examiner

BIPHASIC INJECTABLE ELECTRODE

CROSS-REFERENCE TO RELATED APPLICATION

This application claims the benefit of priority under 35 U.S.C. § 119 to Great Britain Patent Application No. GB 2103132.3, entitled "BIPHASIC INJECTABLE ELECTRODE," filed on Mar. 5, 2021, the disclosure of which is incorporated by reference herein in its entirety.

FIELD

The present invention relates to a biphasic injectable electrode. More specifically the present invention relates to a biphasic injectable electrode which comprises a plurality of solid particles and a transporter phase, wherein both the solid particles and the transporter phase comprise poly(3,4-ethylenedioxythiophene)polystyrene sulfonate, and for its use in the electrotherapy treatment of diseases.

BACKGROUND

According to the National Cancer Institute, solid tumors are "an abnormal mass of tissue that results when cells divide more than they should or do not die when they should." They can occur in several places e.g., bones, muscles and organs, and can be benign or malignant. Different types of solid tumors are named for the type of cells that form them e.g., sarcomas, carcinomas, and lymphomas, and treatment generally combines several types of treatment including surgery, chemotherapy and radiation therapy.

Surgical resection of a tumor is a procedure undertaken to remove the tumor and, if necessary, some additional normal tissue surrounding it. Partial surgical resection (sometimes called debulking) of tumors, particularly malignant tumors, is a sub-form of this procedure whereby a surgically incurable tumor is partially removed, in order to make subsequent therapy with chemotherapy, radiation or other adjunctive measures more effective and improve the length of survival. Partial surgical resection is undertaken clinically for several cancers including cancer of the testis and ovary, lymphoma, sarcoma, renal cell carcinoma, adrenal and other endocrine-related tumors, cancers of the central nervous system for example glioblastoma multiforme, and other solid tumors.

The aim of tumor surgical resection is to excise the maximum amount of tumor that is safe to remove. It leaves behind an empty cavity that varies in size, geometry and location from patient to patient. It can be extremely difficult to differentiate between the cancer and healthy tissue during surgery and it is inevitable that residual cancer cells are left behind in the surrounding tissue—these are referred to as the tumor resection margins (TRMs). This is a particular problem in grade IV gliomas—glioblastoma multiforme (GBM).

Electrotherapy has been demonstrated to be an effective treatment for GBM. In phase III multi-center clinical trials, electrotherapy has been shown to increase patient overall survival to 21 months when used as an addition to surgery, chemotherapy and radiotherapy (Stupp et al.; JAMA; 2017; 318(23):2306-16; doi: 10.1001/jama.2017.18718.). This is achieved by delivering alternating sinusoidal electrical fields at specific frequencies (50-300 kHz) to the head. At these frequencies, electrical fields have been shown to interfere with cancer cell mitosis, thereby slowing the growth of recurrent tumors and extending patient survival (Kirson et al.; PNAS; 2007; 104(24):10152-7; doi:10.1073/pnas.0702916104).

At present, there is only one electrotherapy device in clinical use for cancer treatment. In this device, the therapeutic electrical fields are delivered to the patient's head by the means of transducer arrays affixed to the scalp. These transducers are connected to an external battery and stimulator pack that the patients must carry around with them and the recommended daily treatment period is 18 hours per day. However, there are several problems with this external stimulation approach. Firstly, the electrical fields generated at the center of the brain (where the tumor resection margins are located) are exponentially weaker than those at the skin surface where the electric field is being generated which limits treatment efficacy. In order to account for this and ensure an electrical field of effective strength is generated at the treatment site, a large heavy battery is used resulting in a highly cumbersome device which impacts patient independence and mobility. Furthermore, the transducers affixed to the scalp are highly conspicuous, take approximately 50 minutes to apply to the head each morning and require the patient's head to be shaved every two days. This greatly impacts a patient's quality of life, and the continuous placement of the transducers of the scalp can cause severe skin irritation and resultant pain as a consequence of the large electrical currents that are crossing the skin. These impacts on patient's quality of life mean only a small percentage of patients comply with the recommended daily dosing time (Toms et al.; Journal of Neuro-Oncology; 2019; 141(2):467-473; doi:10.1007/s11060-018-03057-z). There is a clear correlation between amount of time each day GBM patients are receiving electrotherapy and overall survival, with the data strongly suggestive that continuous (24 h/day) treatment would result in the greatest overall survival, so the issues with patient compliance is directly limiting the treatment efficacy.

In order to be more effective, electrotherapy following tumor resection has to overcome several challenges. Firstly, the presence of the void space (created by surgery) presents a resistive barrier, decreasing the effective electrical field strength at the TRMs. Secondly, residual cancer cells reside 3-dimensionally in any direction from the center of the resection cavity. Thirdly, whilst estimates can be made based on pre-operative scans, the precise size and geometry of the cavity is not known until during the procedure. Fourthly, any surgery carries a degree of risk to the patient, and is expensive, so ideally implantation of an electrotherapy device should take place during the existing tumor resection surgery. Fifthly, many patients will be treated by radiotherapy after resection surgery. Tissue often temporarily swells immediately after radiotherapy treatment, and the dimensions of the tumor resection cavity shrinks. Anything that would restrict the ability of the cavity to shrink, for example the introduction of a hard-implanted electrode, could have fatal consequences in organs like the brain as a result of increased intracranial pressure. Finally, any implanted electrode would be expected to remain in situ for the remainder of the life of the patient (which could be several years) so the materials must be biocompatibility and not cause adverse reactions. Biocompatibility requirements apply to both the materials as implanted and their evolution over time, including any degradation products. All products must be non-toxic and non-pyrogenic, and should not release any ionic species into the tissue as a result of corrosion reactions with the tissue fluid. These reactions can be exacerbated by electrical fields which supply the activation energy required for many corrosion reactions; and the resultant release of ionic species can be cytotoxic and pro-inflammatory. Biocompatibility requirements also include the mechanical properties of the electrode itself; brain tissue for example is incredibly soft, in the order of <2 kPa, and any introduction of mechanically mismatched harder materials could result in localized scarring and other adverse biological reactions. It is therefore desirable for the materials utilized to be on the same order of magnitude of stiffness as the host tissue or softer.

A further issue that needs to be managed with any proposed electrotherapy device is that there are two families of mechanisms of charge transfer by which electrical stimulation can be delivered from an electrode to the treatment area: Faradaic and capacitive charge transfer. Faradaic charge transfer mechanisms cause localized changes in the chemical makeup of the electrolyte, and are associated with tissue damage and the degradation of the electrode (SF Cogan; Neural Stimulation and recording electrodes; Annual Review of Biomedical Engineering; 2008). Accordingly, in order to ensure good performance, biocompatibility and the long-functioning of an implanted electrotherapy device, it is necessary to employ electrodes that will be able to deliver large amounts of charge under a capacitive charge injection regime in the body. Capacitive charge injection does not result in the release of any chemical species into the tissue and therefore has much less potential to cause harm, but it also typically delivers approximately 10× lower current into the surrounding tissue when compared to a Faradaic charge injection regime at the same applied voltage. This can be countered by the application of a higher voltage for capacitive charge injection systems.

WO 2018/227165 describes an electrode cured and manufactured in the body, and related methods and devices and WO 2018/111949 describes an electrode curable and moldable to contours of a target in bodily tissue and methods of manufacturing and placement and dispensers therefore. Neither application disclose biphasic injectable electrodes comprising poly(3,4-ethylenedioxythiophene)polystyrene sulfonate in both phases.

The present description discloses a biphasic injectable electrode that overcomes these challenges and the disadvantages of current electrotherapy. The biphasic injectable electrode of the present disclosure can assume the shape and volume of the cavity it resides in, interfacing directly with the TRMs, and allows for the three-dimensional generation of electrical fields. Furthermore, these electrodes can respond dynamically to any changes in the size of the tumor cavity and remain in direct contact with the walls of the TRMs at all times. Delivery of electrical fields from within the tumor resection cavity results in higher electrical field strengths at the TRM, which should result in improved patient outcomes. Furthermore, this approach removes the problem of painful skin irritation experienced with the existing device described above (there is no sensation from within brain tissue for example). Finally, injectable electrode technology would allow for continuous electrotherapy, which could significantly improve patient outcomes.

The properties of the biphasic injectable electrodes described herein also have benefits for the accompanying device needed to deliver the charge. As a result of the focal application of the electrical fields, an exponentially lower voltage is required to generate the same electrical field strengths than with the existing device. Use of lower voltages enables the usage of smaller batteries (which last longer), and enables the device to be miniaturized and implanted. By entirely implanting the device, it is possible to overcome several issues—there is nothing visible outside of the body, nothing cumbersome to carry around, (and for brain tumors) no head shaving required.

SUMMARY

This specification describes, in part, a biphasic injectable electrode which comprises a plurality of solid particles and a transporter phase, wherein both the solid particles and the transporter phase comprise poly(3,4-ethylenedioxythiophene)polystyrene sulfonate.

This specification also describes, in part, a biphasic injectable electrode which comprises a plurality of solid particles and a transporter phase, wherein both the solid particles and the transporter phase comprise poly(3,4-ethylenedioxythiophene)polystyrene sulfonate for use in therapy.

This specification also describes, in part, a biphasic injectable electrode which comprises a plurality of solid particles and a transporter phase, wherein both the solid particles and the transporter phase comprise poly(3,4-ethylenedioxythiophene)polystyrene sulfonate for use in electrotherapy.

This specification also describes, in part, a method of treatment in a warm-blooded animal, such as man, which comprises administering electrotherapy to said animal comprising a biphasic injectable electrode which comprises a plurality of solid particles and a transporter phase, wherein both the solid particles and the transporter phase comprise poly(3,4-ethylenedioxythiophene)polystyrene sulfonate.

This specification also describes, in part, an apparatus for use in electrotherapy, comprising a biphasic injectable electrode which comprises a plurality of solid particles and a transporter phase, wherein both the solid particles and the transporter phase comprise poly(3,4-ethylenedioxythiophene)polystyrene sulfonate, a counter electrode, a probe and a charge delivery device.

This specification also describes, in part, a kit comprising:
a) a biphasic injectable electrode which comprises a plurality of solid particles and a transporter phase, wherein both the solid particles and the transporter phase comprise poly(3,4-ethylenedioxythiophene) polystyrene sulfonate;
b) a counter electrode;
c) a probe; and
d) a charge delivery device.

BRIEF DESCRIPTION OF THE DRAWINGS

The drawings illustrate generally, by way of example, but not by way of limitation, various embodiments discussed in the present document.

DETAILED DESCRIPTION

Figure 1:
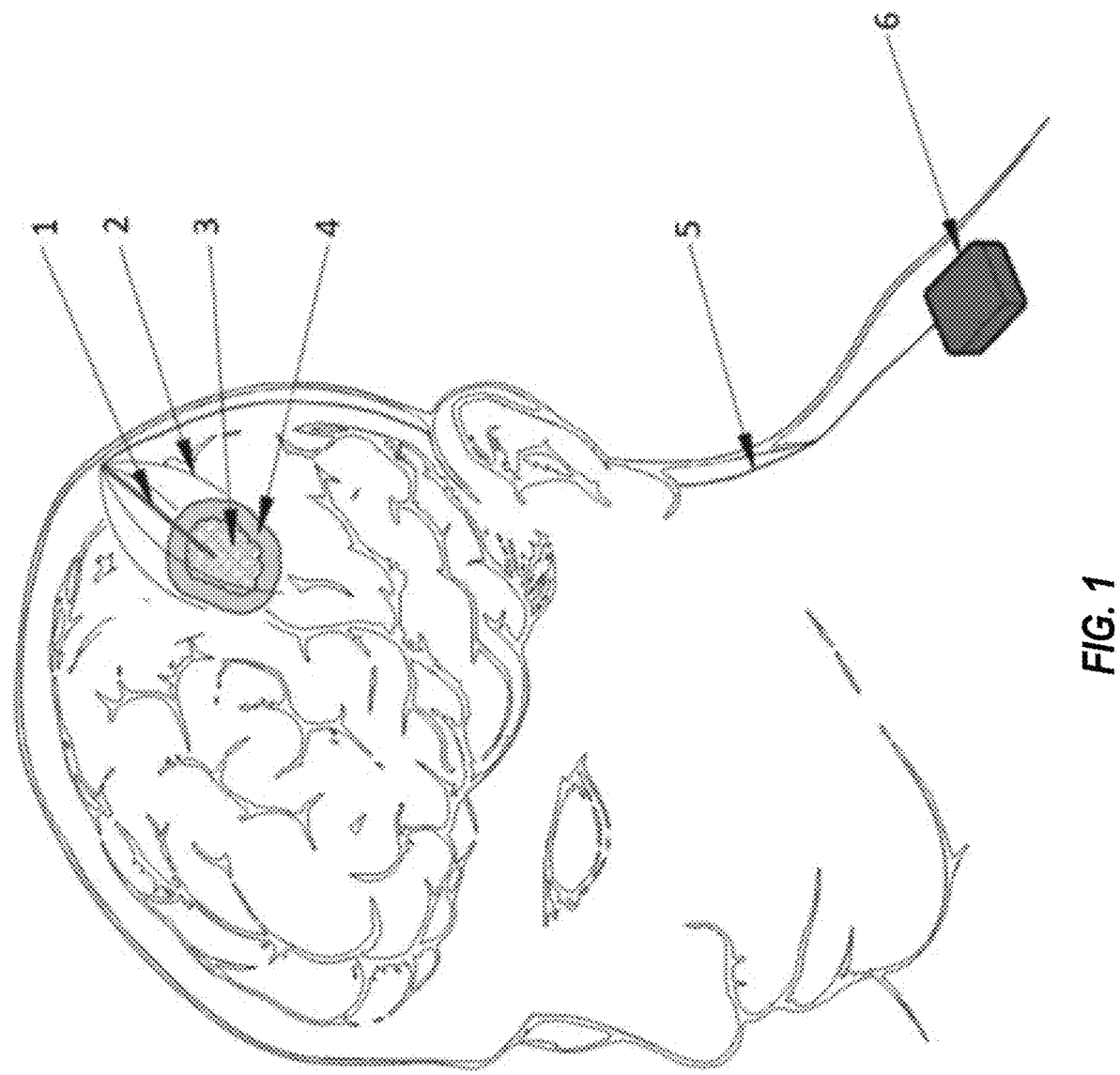
FIG. 1 is a transparent view of a biphasic injectable electrode as described herein, in use in a surgical resection cavity in the brain. The charge delivery apparatus is also shown. A biphasic injectable electrode (3) is inserted into a surgical resection cavity in the brain with a tumor resection margin (4). A probe (1) is inserted into the electrode and four counter electrodes (2) are implanted in the surrounding brain tissue. A charge delivery device (6) has been surgically implanted and delivers charge to the probe via a wire (5) which has also been implanted.

Many embodiments of the invention are detailed throughout the specification and will be apparent to a reader skilled in the art. The invention is not to be interpreted as being limited to any of the recited embodiments.

"A" means "at least one". In any embodiment where "a" is used to denote a given material or element, "a" may mean one.

"Comprising" means that a given material or element may contain other materials or elements. In any embodiment where "comprising" is mentioned the given material or element may be formed of at least 10% w/w, at least 20% w/w, at least 30% w/w, or at least 40% w/w of the material or element. In any embodiment where "comprising" is mentioned, "comprising" may also mean "consisting of (or "consists of") or "consisting essentially of" (or "consists essentially of") a given material or element.

"Consisting of" or "consists of" means that a given material or element is formed entirely of the material or element. In any embodiment where "consisting of" or "consists of" is mentioned the given material or element may be formed of 100% w/w of the material or element.

"Consisting essentially of" or "consists essentially of" means that a given material or element consists almost entirely of that material or element. In any embodiment where "consisting essentially of" or "consists essentially of" is mentioned the given material or element may be formed of at least 50% w/w, at least 60% w/w, at least 70% w/w, at least 80% w/w, at least 90% w/w, at least 95% w/w or at least 99% w/w of the material or element.

In any embodiment where "is" or "may be" is used to define a material or element, "is" or "may be" may mean the material or element "consists of" or "consists essentially of" the material or element.

Claims are embodiments.

Embodiments may be combined.

Injectable

The present specification describes a biphasic injectable electrode, as described herein, capable of interfacing with tissue, particularly human tissue, and filling a surgical cavity of unknown geometry. A biphasic injectable electrode, as described herein, is one that may be introduced via injection.

In one embodiment the biphasic injectable electrode, as described herein, may be suitable for introduction into a cavity under pressure.

In one embodiment the biphasic injectable electrode, as described herein, may be suitable for introduction into a cavity created by surgery under pressure.

In one embodiment the biphasic injectable electrode, as described herein, may be suitable for introduction into a cavity via injection.

In one embodiment the biphasic injectable electrode, as described herein, may be suitable for introduction into a cavity created by surgery via injection.

In one embodiment the biphasic injectable electrode, as described herein, may be suitable for introduction into a cavity via a syringe.

In one embodiment the biphasic injectable electrode, as described herein, may be suitable for introduction into a cavity created by surgery via a syringe.

Electrode

An electrode is a conductor that delivers and receives an electrical current from one medium to another. Electrodes may be used for the purpose of delivering electrical currents between charge delivery devices and the human body.

Poly(3,4-ethylenedioxythiophene)polystyrene Sulfonate

Poly(3,4-ethylenedioxythiophene)polystyrene sulfonate (PEDOT:PSS) is a conductive polymer mixture of sodium polystyrene sulfonate and poly(3,4-ethylenedioxythiophene) (PEDOT).

Biphasic

A biphasic injectable electrode as described herein, comprises at least two phases—the solid phase comprising a plurality of solid particles and the transporter phase.

In one embodiment the biphasic injectable electrode comprises two phases.

In one embodiment the biphasic injectable electrode comprises more than two phases.

Solid Particles

The biphasic injectable electrode, as described herein, comprises a plurality of solid particles which comprises poly(3,4-ethylenedioxythiophene)polystyrene sulfonate. The solid particles are solids in that they retain their shape and do not flow either under steady state conditions, or in response to the applied shear force of injection. The solid particles are injectable in nature because of the size and shape of the particles, which are small enough to be injectable via syringe. These solid particles are distributed within the transporter phase. The solid particles have excellent electrical conductivity owing to their dense network of poly(3,4-ethylenedioxythiophene)polystyrene sulfonate chains, but rely on the flowability of the transporter phase to create an electrode that is easily injectable.

In one embodiment the solid particles comprise a gel. A gel is a non-fluid colloidal network of particles, polymers or other molecules that is expanded throughout its volume by a fluid, but does not flow.

In one embodiment the solid particles consist of a gel.

In one embodiment the solid particles consist essentially of a gel.

In one embodiment the solid particles comprise a non-shear thinning gel.

In one embodiment the solid particles consist of a non-shear thinning gel.

In one embodiment the solid particles consist essentially of a non-shear thinning gel.

In one embodiment the solid particles comprise a plurality of solid particles small enough to be injectable via syringe.

In one embodiment the solid particles comprise a plurality of solid particles with a maximum dimension of 4 mm.

In one embodiment the solid particles comprise a plurality of solid particles with a maximum dimension of 1.5 mm.

In one embodiment the solid particles comprise a plurality of solid particles with a minimum dimension of 0.1 mm.

In one embodiment the solid particles comprise a plurality of solid particles with dimensions of 0.1-1.5 mm.

In one embodiment the solid particles comprise a plurality of solid particles with dimensions of 0.1-4 mm.

In one embodiment the solid particles comprise a plurality of solid particles with dimensions of 1-4 mm.

In one embodiment the solid particles comprise a plurality of solid particles with dimensions of about 1-4 mm.

In one embodiment the solid particles comprise a plurality of solid particles with dimensions of about 1 mm.

In one embodiment, the solid particles comprise 40-85% v/v of the injectable electrode.

In one embodiment, the solid particles comprise 60-85% v/v of the injectable electrode.

In one embodiment, the solid particles comprise 40% v/v of the injectable electrode.

In one embodiment, the solid particles comprise 50% v/v of the injectable electrode.

In one embodiment, the solid particles comprise 60% v/v of the injectable electrode.

In one embodiment, the solid particles comprise 70% v/v of the injectable electrode.

In one embodiment, the solid particles comprise 75% v/v of the injectable electrode.

In one embodiment, the solid particles comprise 80% v/v of the injectable electrode.

In one embodiment, the solid particles comprise 85% v/v of the injectable electrode.

In one embodiment, the solid particles comprise about 40-50% v/v of the injectable electrode.

In one embodiment, the solid particles comprise about 50-60% v/v of the injectable electrode.

In one embodiment, the solid particles comprise about 60-70% v/v of the injectable electrode.

In one embodiment, the solid particles comprise about 70-80% v/v of the injectable electrode.

In one embodiment, the solid particles comprise about 75-85% v/v of the injectable electrode.

In one embodiment, the solid particles comprise about 80-90% v/v of the injectable electrode.

In one embodiment, the solid particles comprise about 85-95% v/v of the injectable electrode.

In one embodiment, the solid particles comprise at least 90% v/v poly(3,4-ethylenedioxythiophene)polystyrene sulfonate.

In one embodiment, the solid particles comprise at least 95% v/v poly(3,4-ethylenedioxythiophene)polystyrene sulfonate.

In one embodiment, the solid particles comprise poly(3,4-ethylenedioxythiophene)polystyrene sulfonate.

In one embodiment, the solid particles consist essentially of poly(3,4-ethylenedioxythiophene)polystyrene sulfonate.

In one embodiment, the solid particles consist of poly(3,4-ethylenedioxythiophene)polystyrene sulfonate.

Transporter Phase

The biphasic injectable electrode, as described herein, comprises a transporter phase which comprises poly(3,4-ethylenedioxythiophene)polystyrene sulfonate. The transporter phase of the biphasic injectable electrode allows for precise volume of the cavity (regardless of patient-patient differences) to be filled in a matter of seconds. This results in tight electrical contact with the resection walls, and the speed of injections ensures there is no significant lengthening of the surgery (important for patient safety). The transporter phase of the biphasic injectable electrode comprises a substance that can flow either under steady state conditions, or in response to the applied sheer force of injection, for example a shear thinning gel or a viscous liquid, but should not significantly diffuse into the surrounding tissue—diffusion into the surrounding tissue could potentially lead to biocompatibility problems and/or destabilize the transporter phase. "Shear thinning" describes the non-Newtonian behavior of fluids whose viscosity decreases under shear strain. The poly(3,4-ethylenedioxythiophene)polystyrene sulfonate in the transporter phase is solubilized. The less dense molecular network of poly(3,4-ethylenedioxythiophene)polystyrene sulfonate in the transporter phase confers some electrical conductivity but relatively less than the solid particles. The key function of the transporter phase is to assist with flowability and create an electrode that is easily injectable.

In one embodiment, the transporter phase should be resistant to dissolution.

In one embodiment the transporter phase comprises a viscous liquid.

In one embodiment the transporter phase consists of a viscous liquid.

In one embodiment the transporter phase consists essentially of a viscous liquid.

In one embodiment the transporter phase comprises a shear thinning gel.

In one embodiment the transporter phase consists of a shear thinning gel.

In one embodiment the transporter phase consists essentially of a shear thinning gel.

In one embodiment the transporter phase comprises 15-60% v/v of the injectable electrode.

In one embodiment the transporter phase comprises 15-40% v/v of the injectable electrode.

In one embodiment, the transporter phase comprises 60% v/v of the injectable electrode.

In one embodiment, the transporter phase comprises 50% v/v of the injectable electrode.

In one embodiment, the transporter phase comprises 40% v/v of the injectable electrode.

In one embodiment, the transporter phase comprises 30% v/v of the injectable electrode.

In one embodiment, the transporter phase comprises 25% v/v of the injectable electrode.

In one embodiment, the transporter phase comprises 20% v/v of the injectable electrode.

In one embodiment, the transporter phase comprises 15% v/v of the injectable electrode.

In one embodiment, the transporter phase comprises 60-70% v/v of the injectable electrode.

In one embodiment, the transporter phase comprises 50-60% v/v of the injectable electrode.

In one embodiment, the transporter phase comprises 40-50% v/v of the injectable electrode.

In one embodiment, the transporter phase comprises 30-40% v/v of the injectable electrode.

In one embodiment, the transporter phase comprises 20-30% v/v of the injectable electrode.

In one embodiment, the transporter phase comprises 15-25% v/v of the injectable electrode.

In one embodiment, the transporter phase comprises 10-20% v/v of the injectable electrode.

In one embodiment, the transporter phase comprises 5-15% v/v of the injectable electrode.

In one embodiment, the transporter phase comprises <5% v/v poly(3,4-ethylenedioxythiophene)polystyrene sulfonate.

In one embodiment, the transporter phase comprises 0.05-0.25% v/v poly(3,4-ethylenedioxythiophene)polystyrene sulfonate.

In one embodiment, the transporter phase comprises about 0.15% v/v poly(3,4-ethylenedioxythiophene)polystyrene sulfonate.

In one embodiment, the transporter phase comprises 0.15% v/v poly(3,4-ethylenedioxythiophene)polystyrene sulfonate.

In one embodiment, the transporter phase comprises a polymer capable of undergoing partial cross-linking after injection. This could be via UV cross-linking, temperature dependent cross linking (e.g., cross linking that occurs at body temperature), and/or salt-dependent cross-linking. Partial cross-linking after injection may assist in stabilizing the transporter phase.

Additional Components

The transporter phase and the solid particles of the biphasic injectable electrode, as described herein, may consist of poly(3,4-ethylenedioxythiophene)polystyrene sulfonate alone, or as a mixture or composite with other materials such as clay, polyethylene glycol (PEG), polyvinyl alcohol (PVA), polydimethylsiloxane (PDMS), xanthan gum, (3-glycidyloxypropyl)trimethoxysilane, ethylene glycol, dodecylbenzenesulfonic acid, cyclodextrin and/or polyvinylamine, or as a mixture or composite with other materials such as clay, polyethylene glycol (PEG), poly(ethylene glycol) methacrylate, poly(ethylene glycol)diacrylate, polyvinyl alcohol (PVA), polydimethylsiloxane (PDMS), xanthan gum, (3-glycidyloxypropyl)trimethoxysilane, ethylene glycol, dodecylbenzenesulfonic acid, methylcellulose, hydroxymethylcellulose, guar gum, Pluronic F-127, poly(N-isopropylacrylamide) (PNIPAAM), kappa-carrageenan, cyclodextrin, phosphate-buffered saline (PBS) and/or polyvinylamine.

A mixture is a material made from two or more materials where the constituent materials are fully distributed within the whole. The distribution is random with no defined structure.

A composite is a material made from two or more materials with significantly different physical or chemical properties that, when combined, produce a material with characteristics different from the individual components. These constituent materials may have a defined structure and organization within the whole. The distribution of these defined structures of the constituent materials within the whole, may confer properties on the composite material that would not be present in a random mixture of the two materials.

Clay is a material formed from layered silicates, which may also be complexed to metals and metal oxides, including species formed from aluminum, iron, magnesium and sodium. In any embodiment where clay is mentioned, this may refer to hectorite. Hectorite is a soft, greasy, white clay mineral with a chemical formula of $Na_{0.3}(Mg,Li)_3Si_4O_{10}(OH)_2$. In any embodiment where clay is mentioned, this may refer to clay nanoparticles. In any embodiment where clay is mentioned, this may refer to smectite clay, particularly smectite clay nanoparticles, comprising magnesium oxide and silica, for example Laponite®. Laponite is a synthetic smectite clay with a structure and composition closely resembling the natural clay mineral hectorite. It is a layered hydrous magnesium silicate belonging to the family of (2:1) phyllosilicates and is built up of sheets of octahedrally coordinated magnesium oxide sandwiched between two parallel sheets of tetrahedrally coordinated silica.

Polyethylene glycol (PEG) is a synthetic polymer made by polymerizing ethylene glycol.

Poly(ethylene glycol) methacrylate is a diester formed by condensation of methacrylic acid and ethylene glycol.

Polyethylene glycol diacrylate is a long-chain, hydrophilic, crosslinking monomer.

Polyvinyl alcohol (PVA) is a water-soluble synthetic polymer prepared by the hydrolysis of polyvinyl acetate.

Polydimethylsiloxane (PDMS) is a non-toxic dimethyl silicone-based organic polymer which belongs to a group of polymeric organosilicone compounds known as silicones.

Xanthan gum is a substance produced by bacterial fermentation or synthetically and used in foods as a gelling agent and thickener. It is a polysaccharide composed of glucose, mannose, and glucuronic acid.

Methylcellulose and hydroxymethylcellulose are cellulose esters that are derived from cellulosic materials for instance natural wood or cotton linters. It is typically used as a thickener and emulsifier in various food and cosmetic products. Water soluble methylcellulose is obtained by treatment with sodium hydroxide, methyl chloride and/or propylene oxide.

Guar gum is extracted from guar beans and is commonly used thickening and stabilizing agent in the food industry.

Pluronic F-127 is a non-ionic copolymer surfactant that is made of amphiphilic copolymers ethylene oxide and polypropylene oxide.

Kappa-carrageenan is part of a natural linear sulphated polysaccharide family carrageenan's and is extracted from specific red seaweed species. It is typically used as stabilizer, thickener and gelling agent.

Cyclodextrins are a family of cyclic oligosaccharides. They are macrocyclic ring of glucose subunits joined by α-1,4 glycosidic bonds. Cyclodextrins may be produced from starch by enzymatic conversion. Cyclodextrins are composed of 5 or more α-D-glucopyranoside units linked 1->4, as in amylose (a fragment of starch).

Polyvinylamine is a polymer typically produced through the polymerization of N-vinylformamide. It comprises repeating monomers of vinylamine.

In one embodiment a biphasic injectable electrode, as described herein, may additionally comprise clay, polyethylene glycol (PEG), polyvinyl alcohol (PVA), polydimethylsiloxane (PDMS), xanthan gum, (3-glycidyloxypropyl)trimethoxysilane, ethylene glycol, dodecylbenzenesulfonic acid, cyclodextrin and/or polyvinylamine.

In one embodiment a biphasic injectable electrode, as described herein, may additionally comprise clay.

In one embodiment a biphasic injectable electrode, as described herein, may additionally comprise polyethylene glycol (PEG).

In one embodiment a biphasic injectable electrode, as described herein, may additionally comprise poly(ethylene glycol) methacrylate.

In one embodiment a biphasic injectable electrode, as described herein, may additionally comprise polyethylene glycol diacrylate.

In one embodiment a biphasic injectable electrode, as described herein, may additionally comprise polyvinyl alcohol (PVA).

In one embodiment a biphasic injectable electrode, as described herein, may additionally comprise polydimethylsiloxane (PDMS).

In one embodiment a biphasic injectable electrode, as described herein, may additionally comprise xanthan gum.

In one embodiment a biphasic injectable electrode, as described herein, may additionally comprise (3-glycidyloxypropyl)trimethoxysilane.

In one embodiment a biphasic injectable electrode, as described herein, may additionally comprise ethylene glycol.

In one embodiment a biphasic injectable electrode, as described herein, may additionally comprise dodecylbenzenesulfonic acid.

In one embodiment a biphasic injectable electrode, as described herein, may additionally comprise methylcellulose.

In one embodiment a biphasic injectable electrode, as described herein, may additionally comprise hydroxymethylcellulose.

In one embodiment a biphasic injectable electrode, as described herein, may additionally comprise methylcellulose and hydroxymethylcellulose.

In one embodiment a biphasic injectable electrode, as described herein, may additionally comprise guar gum.

In one embodiment a biphasic injectable electrode, as described herein, may additionally comprise Pluronic F-127.

In one embodiment a biphasic injectable electrode, as described herein, may additionally comprise phosphate-buffered saline.

In one embodiment a biphasic injectable electrode, as described herein, may additionally comprise kappa-carrageenan.

In one embodiment a biphasic injectable electrode, as described herein, may additionally comprise cyclodextrin.

In one embodiment a biphasic injectable electrode, as described herein, may additionally comprise polyvinylamine.

In one embodiment the solid particles comprise poly(3,4-ethylenedioxythiophene)polystyrene sulfonate and polyvinyl alcohol (PVA), (3-glycidyloxypropyl)trimethoxysilane and/or ethylene glycol.

In one embodiment the transporter phase further comprises clay, polyethylene glycol (PEG), poly(ethylene glycol) methacrylate, poly(ethylene glycol)diacrylate, polyvinyl alcohol (PVA), polydimethylsiloxane (PDMS), xanthan gum, (3-glycidyloxypropyl)trimethoxysilane, ethylene glycol, dodecylbenzenesulfonic acid, methylcellulose, hydroxymethylcellulose, guar gum, Pluronic F-127, poly(N-isopropylacrylamide) (PNIPAAM), kappa-carrageenan, cyclodextrin, phosphate-buffered saline (PBS) and/or polyvinylamine.

In one embodiment the transporter phase comprises poly(3,4-ethylenedioxythiophene)polystyrene sulfonate and clay, polyethylene glycol (PEG), polyvinyl alcohol (PVA), polydimethylsiloxane (PDMS), xanthan gum, (3-glycidyloxypropyl)trimethoxysilane and/or ethylene glycol.

In one embodiment the transporter phase comprises poly(3,4-ethylenedioxythiophene)polystyrene sulfonate and polyvinyl alcohol (PVA), (3-glycidyloxypropyl)trimethoxysilane and/or ethylene glycol.

In one embodiment the transporter phase, as described herein, may additionally comprise clay, polyethylene glycol (PEG), polyvinyl alcohol (PVA), polydimethylsiloxane (PDMS), xanthan gum, (3-glycidyloxypropyl)trimethoxysilane, ethylene glycol, dodecylbenzenesulfonic acid, cyclodextrin and/or polyvinylamine.

In one embodiment the transporter phase, as described herein, may additionally comprise clay.

In one embodiment the transporter phase, as described herein, may additionally comprise polyethylene glycol (PEG).

In one embodiment the transporter phase, as described herein, may additionally comprise poly(ethylene glycol) methacrylate.

In one embodiment the transporter phase, as described herein, may additionally comprise polyethylene glycol diacrylate.

In one embodiment the transporter phase, as described herein, may additionally comprise polyvinyl alcohol (PVA).

In one embodiment the transporter phase, as described herein, may additionally comprise polydimethylsiloxane (PDMS).

In one embodiment the transporter phase, as described herein, may additionally comprise xanthan gum.

In one embodiment the transporter phase, as described herein, may additionally comprise (3-glycidyloxypropyl)trimethoxysilane.

In one embodiment the transporter phase, as described herein, may additionally comprise ethylene glycol.

In one embodiment the transporter phase, as described herein, may additionally comprise dodecylbenzenesulfonic acid.

In one embodiment the transporter phase, as described herein, may additionally comprise methylcellulose.

In one embodiment the transporter phase, as described herein, may additionally comprise 5-10% w/v methylcellulose.

In one embodiment the transporter phase, as described herein, may additionally comprise 7-9% w/v methylcellulose.

In one embodiment the transporter phase, as described herein, may additionally comprise about 8% w/v methylcellulose.

In one embodiment the transporter phase, as described herein, may additionally comprise 8% w/v methylcellulose.

In one embodiment the transporter phase, as described herein, may additionally comprise hydroxymethylcellulose.

In one embodiment the transporter phase, as described herein, may additionally comprise methylcellulose and hydroxymethylcellulose.

In one embodiment the transporter phase, as described herein, may additionally comprise guar gum.

In one embodiment the transporter phase, as described herein, may additionally comprise Pluronic F-127.

In one embodiment the transporter phase, as described herein, may additionally comprise phosphate-buffered saline.

In one embodiment the transporter phase, as described herein, may additionally comprise 0.5-5% v/v phosphate-buffered saline.

In one embodiment the transporter phase, as described herein, may additionally comprise 0.5-3% v/v phosphate-buffered saline.

In one embodiment the transporter phase, as described herein, may additionally comprise about 1% v/v phosphate-buffered saline.

In one embodiment the transporter phase, as described herein, may additionally comprise 1% v/v phosphate-buffered saline.

In one embodiment the transporter phase, as described herein, may additionally comprise kappa-carrageenan.

In one embodiment the transporter phase, as described herein, may additionally comprise cyclodextrin.

In one embodiment the transporter phase, as described herein, may additionally comprise polyvinylamine.

In one embodiment the transporter phase, as described herein, comprises methylcellulose, poly(3,4-ethylenedioxythiophene)polystyrene sulfonate, phosphate-buffered saline and water.

In one embodiment the transporter phase, as described herein, consists essentially of methylcellulose, poly(3,4-ethylenedioxythiophene)polystyrene sulfonate, phosphate-buffered saline and water.

In one embodiment the transporter phase, as described herein, consists of methylcellulose, poly(3,4-ethylenedioxythiophene)polystyrene sulfonate, phosphate-buffered saline and water.

In one embodiment the transporter phase, as described herein, comprises:
  65-85% v/v 10% w/v methylcellulose;
  10-20% v/v 1% w/v poly(3,4-ethylenedioxythiophene) polystyrene sulfonate; and
  5-15% v/v 10× phosphate-buffered saline.

The phrase "65-85% v/v 10% w/v methylcellulose" means the transporter phase contains 65-85% v/v of a 10% w/v solution of methylcellulose in water. The phrase "10-20% v/v 1% w/v poly(3,4-ethylenedioxythiophene)polystyrene sulfonate" means the transporter phase contains 10-20% v/v of a 1% w/v solution of poly(3,4-ethylenedioxythiophene) polystyrene sulfonate in water. 10× phosphate-buffered saline is a standard isotonic solution, for example one comprising 1.37 M NaCl, 27 mM KCl, 100 mM $Na_2HPO_4$, and 18 mM $KH_2PO_4$.

In one embodiment the transporter phase, as described herein, comprises:
  about 75% v/v 10% w/v methylcellulose;
  about 15% v/v 1% w/v poly(3,4-ethylenedioxythiophene) polystyrene sulfonate; and
  about 10% v/v 10× phosphate-buffered saline.

In one embodiment the transporter phase, as described herein, comprises:
  75% v/v 10% w/v methylcellulose;
  15% v/v 1% w/v poly(3,4-ethylenedioxythiophene)polystyrene sulfonate; and
  10% v/v 10× phosphate-buffered saline.

Soft

In one embodiment the biphasic injectable electrode, as described herein, may be a soft biphasic injectable electrode. In one embodiment, where the biphasic injectable electrode, as described herein, is to be used in the brain it may be soft, with elastic moduli equivalent to those of the brain tissue. Ensuring the biphasic injectable electrode, as described herein, does not have significantly higher stiffness than the brain tissue, aids its ability to respond dynamically to tissue swelling (maintaining contact with the cavity walls).

In one embodiment the storage modulus of the biphasic injectable electrode, as described herein, is <5 kPa at an oscillation strain of 0.1% when assessed by oscillatory rheometry at a temperature of 37° C. and a frequency of 1 Hz.

In one embodiment the storage modulus of the biphasic injectable electrode, as described herein, is <4 kPa at an oscillation strain of 0.1% when assessed by oscillatory rheometry at a temperature of 37° C. and a frequency of 1 Hz.

In one embodiment the storage modulus of the biphasic injectable electrode, as described herein, is <3 kPa at an oscillation strain of 0.1% when assessed by oscillatory rheometry at a temperature of 37° C. and a frequency of 1 Hz.

In one embodiment the storage modulus of the biphasic injectable electrode, as described herein, is <2 kPa at an oscillation strain of 0.1% when assessed by oscillatory rheometry at a temperature of 37° C. and a frequency of 1 Hz.

In one embodiment the storage modulus of the biphasic injectable electrode, as described herein, is 0.1-2 kPa at an oscillation strain of 0.1% when assessed by oscillatory rheometry at a temperature of 37° C. and a frequency of 1 Hz.

High Levels of Charge Injection

In one embodiment the biphasic injectable electrode, as described herein, comprises a material that is capable of delivering high levels of capacitive charge injection without inducing Faradaic reactions.

Capacitive charge injection occurs under an applied voltage in all material-electrolyte interfaces, but in order to prevent Faradaic reactions from taking place it is necessary to ensure that the applied voltage is below the activation voltage of the most reactive Faradaic process in that system. The hydrolysis of water into hydrogen and oxygen occurs at approximately ±1.1V of applied potential; and since all biological tissues are water based, this presents the maximal potential that can be applied under a capacitive charge injection regime for use in implanted medical devices. It is therefore necessary for an electrotherapy implant to be able to apply as high a potential as is safely possible under a capacitive charge injection regime.

In one embodiment the biphasic injectable electrode, as described herein, is capable of delivering ±1V to human tissues under a capacitive charge transfer regime without inducing any Faradaic reactions.

Low Electrical Impedance

In one embodiment the biphasic injectable electrode, as described herein, comprises a material that has low electrical impedance. This ensures efficient transfer of charge from the biphasic injectable electrode to the tissue without introducing undue heating (which would be damaging to tissue).

In one embodiment the biphasic injectable electrode, as described herein, has an interfacial electrical impedance less than 200 ohms when measured by electrochemical impedance spectroscopy at 1000 Hz.

In one embodiment the biphasic injectable electrode, as described herein, has an interfacial electrical impedance less than 250 ohms when measured by electrochemical impedance spectroscopy at 1000 Hz.

In one embodiment the biphasic injectable electrode, as described herein, has an interfacial electrical impedance less than 300 ohms when measured by electrochemical impedance spectroscopy at 1000 Hz.

In one embodiment the biphasic injectable electrode, as described herein, has an interfacial electrical impedance less than 350 ohms when measured by electrochemical impedance spectroscopy at 1000 Hz.

In one embodiment the biphasic injectable electrode, as described herein, has an interfacial electrical impedance of about 350 ohms when measured by electrochemical impedance spectroscopy at 1000 Hz.

Biocompatible

In one embodiment the biphasic injectable electrode, as described herein, comprises a material that is biocompatible. A biocompatible material is important for the avoidance of adverse biological reactions at either acute or chronic time points after implantation.

Use in Electrotherapy

In one embodiment, the electrical charge delivered to the biphasic injectable electrode, as described herein, is supplied by a charge delivery device which may be a stimulator/battery pack. In one embodiment the charge delivery device may be surgically implanted. In one embodiment the charge delivery device may be surgically implanted into the chest cavity. Suitable charge delivery devices include implanted pulse generators (IPGs) for example those used in deep brain stimulation for the alleviation of Parkinson's Disease tremors.

In one embodiment a probe will be inserted into the center of the biphasic injectable electrode, as described herein, in situ, in order to facilitate its connection with the rest of the electronics and complete the circuit. The probe delivers the charge to the biphasic injectable electrode under direct current conditions. Under alternating current conditions, the probe both delivers and receives the charge from the biphasic injectable electrode. This probe may consist of an insulated rod with exposed conductive regions that may contact the biphasic injectable electrode, as described herein. The exposed conductive regions may be manufactured from platinum, a platinum alloy, platinum wire, iridium oxide, a platinum-iridium alloy, carbon, graphene, a conductive polymer and/or a conductive composite. The probe may be connected to the charge delivery device by means of an electrical cable. In one embodiment the electrical cable may be implanted under the skin.

In one embodiment, one or more counter electrodes may be implanted into the tissue surrounding the tumor resection cavity. These complete the electrical circuit and collect the current injected from the biphasic injectable electrode under direct current conditions. Under alternating current conditions, the counter electrodes both receives and delivers the charge to the biphasic injectable electrode. The biphasic injectable electrode and counter electrodes cooperate together. In one embodiment there may be one counter electrode. In one embodiment there may be two counter electrodes. In one embodiment there may be three counter electrodes. In one embodiment there may be four counter electrodes. In one embodiment the counter electrode may comprise platinum, a platinum alloy, platinum wire, iridium oxide, a platinum-iridium alloy, carbon, graphene, a conductive polymer and/or a conductive composite. In one embodiment the counter electrode may comprise platinum. In one embodiment the counter electrode may comprise a platinum alloy. In one embodiment the counter electrode may comprise platinum wire. In one embodiment the counter electrode may comprise iridium oxide. In one embodiment the counter electrode may comprise a platinum-iridium alloy. In one embodiment the counter electrode may comprise carbon. In one embodiment the counter electrode may comprise graphene. In one embodiment the counter electrode may comprise a conductive polymer. In one embodiment the counter electrode may comprise a conductive composite.

In one embodiment there is provided an apparatus for use in electrotherapy, comprising a biphasic injectable electrode, as described herein, a counter electrode, a probe and a charge delivery device. FIG. 1 shows one potential arrangement of this apparatus for use in the brain.

A potential surgical protocol utilizing the biphasic injectable electrode in the treatment of a brain tumor following surgical resection could comprise the following steps:
1. Make a scalp incision & fold back the skin flap
2. Open the cranial window
3. Cut open the dura and resect the tumor
4. Inject the biphasic injectable electrode, as described herein, to fill the resection cavity
5. Suture to close the dura
6. Fit a suitable prosthetic to cover the cranial window
7. Implant central probe into biphasic injectable electrode
8. Implant counter-electrodes
9. Connect probe and counter-electrodes to main lead
10. Replace skin flap and suture closed.

Processes

The solid particles of the biphasic injectable electrode may be manufactured by mixing PEDOT:PSS with DMSO, optionally with the addition of synthetic polymers (for example PVA, PEG, xanthum gum and/or laponite) and/or stabilizers (for example ethylene glycol, DBSA and/or GOPS). The PEDOT:PSS/DMOS/polymer mixture may be cured in a cylindrical mold under heat to form solid sheets of PEDOT:PSS/DMSO/polymer. Excess DMSO may be removed with a series of washes (distilled water, phosphate buffered saline (PBS) and ethanol), and then the sheets are punched out using a spherical punch to form particles of the desired size.

The transporter gel phase of the biphasic injectable electrode may be produced by mixing PEDOT:PSS with DMSO, optionally with the addition of synthetic polymers (for example PVA, PEG, xanthum gum, laponite) and/or stabilizers (for example ethylene glycol, DBSA, GOPS). Alternatively, the transporter phase may be produced by mixing a solution of PEDOT:PSS with solutions of additional ingredients such and methylcellulose and/or phosphate-buffered saline. This solution may be heated with periodic mixing until a gel like/viscous consistency is achieved. Any excess DMSO may be removed from the gel by dialysis using a dialysis membrane with a series of washes in distilled water, PBS and ethanol. After dialysis, synthetic polymers may be added into the gel while heating to improve stability and viscosity of the gel.

The solid particles and transporter phase are mixed together to form the biphasic injectable electrode.

Use

In one embodiment there is provided a biphasic injectable electrode, as described herein, for use in electrotherapy. Electrotherapy is the use of electrical energy as a medical treatment.

In one embodiment there is provided a biphasic injectable electrode for use in therapy which comprises a plurality of solid particles and a transporter phase, wherein both the solid particles and the transporter phase comprise poly(3,4-ethylenedioxythiophene)polystyrene sulfonate.

In one embodiment there is provided a biphasic injectable electrode for use in electrotherapy which comprises a plurality of solid particles and a transporter phase, wherein both the solid particles and the transporter phase comprise poly (3,4-ethylenedioxythiophene)polystyrene sulfonate.

In one embodiment there is provided a biphasic injectable electrode, as described herein, for use in the treatment of solid tumors; deep brain stimulation; spinal cord stimulation; peripheral nerve stimulation; retinal implants for restoration of vision; regeneration of nervous tissue including brain, spinal cord and peripheral nerves; brain/spinal cord/peripheral nerve interfacing; wound healing; the treatment of infection (antibacterial/antiviral/antifungal); or enhancement of drug delivery/gene therapy.

In one embodiment there is provided a biphasic injectable electrode, as described herein, for use in the electrotherapy treatment of:
- brain tumors (including Grade I, II, III or IV glioma; pilocytic astrocytoma; subependymal giant cell astrocytoma; diffuse astrocytoma; oligodendroglioma; oligodendroglioma NOS; anaplastic astrocytoma; anaplastic oligodendroglioma; anaplastic oligodendroglioma NOS; glioblastoma; giant-cell glioblastoma; glioblastoma multiforme; subependymal giant cell astrocytoma; pilomyxoid astrocytoma; pleomorphic xanthoastrocytoma; ganglioglioma; oligoastrocytoma; meningiomas (including grade I, II or III meningioma and other neoplasms related to the meninges (for example haemangiopericytoma)); pediatric brain tumors (including ependymoma, medulloblastoma, atypical teratoid/rhabdoid tumor (AT/RT); choroid plexus papilloma; choroid plexus carcinoma; intracranial teratoma; and embryonal tumors with multilayered rosettes (ETMR)), pineal region tumors (for example pineoblastoma), and pituitary region tumors (for example pituitary adenoma, craniopharyngioma, and chordoma);
- metastases of any cancer origin (for example brain metastasis including those from lung cancer, breast cancer, genitourinary tract cancer, osteosarcoma and melanoma);
- lung cancer (including mesothelioma, malignant pleural mesothelioma, non-small cell-lung cancer and small cell lung cancer)
- pancreatic cancer (for example locally advanced pancreatic adenocarcinoma);
- ovarian cancer (for example ovarian cancer resistant to chemotherapy);
- liver cancer (for example advanced hepatocellular cancer);
- breast cancer;
- cervical cancer;
- colorectal carcinoma;
- gastric cancer (including gastric adenocarcinoma);
- spinal nerve sheath tumors (including schwannoma, neurofibroma and ganglioneuroma);
- malignant melanoma;
- renal adenocarcinoma; and
- urinary transitional cell carcinoma.

In one embodiment there is provided a biphasic injectable electrode, as described herein, for use in the electrotherapy treatment of:
- brain metastases; and
- diffuse midline glioma.

In one embodiment there is provided a biphasic injectable electrode, as described herein, for use in the electrotherapy treatment of solid tumors.

In one embodiment there is provided a biphasic injectable electrode, as described herein, for use in the electrotherapy treatment of a Grade I, II, III or IV glioma.

In one embodiment there is provided a biphasic injectable electrode, as described herein, for use in the electrotherapy treatment of a Grade I glioma.

In one embodiment there is provided a biphasic injectable electrode, as described herein, for use in the electrotherapy treatment of pilocytic astrocytoma.

In one embodiment there is provided a biphasic injectable electrode, as described herein, for use in the electrotherapy treatment of a Grade II glioma.

In one embodiment there is provided a biphasic injectable electrode, as described herein, for use in the electrotherapy treatment of diffuse astrocytoma or oligodendroglioma.

In one embodiment there is provided a biphasic injectable electrode, as described herein, for use in the electrotherapy treatment of a Grade III glioma.

In one embodiment there is provided a biphasic injectable electrode, as described herein, for use in the electrotherapy treatment of anaplastic astrocytoma or anaplastic oligodendroglioma.

In one embodiment there is provided a biphasic injectable electrode, as described herein, for use in the electrotherapy treatment of a Grade IV glioma.

In one embodiment there is provided a biphasic injectable electrode, as described herein, for use in the electrotherapy treatment of diffuse midline glioma.

In one embodiment there is provided a biphasic injectable electrode, as described herein, for use in the electrotherapy treatment of brain metastases.

In one embodiment there is provided a biphasic injectable electrode, as described herein, for use in the electrotherapy treatment of giant-cell glioblastoma or glioblastoma multiforme.

In one embodiment there is provided a biphasic injectable electrode, as described herein, for use in the electrotherapy treatment of glioblastoma multiforme.

In one embodiment there is provided a biphasic injectable electrode, as described herein, for use in the treatment of solid tumors; deep brain stimulation; spinal cord stimulation; peripheral nerve stimulation; retinal implants for restoration of vision; regeneration of nervous tissue including brain, spinal cord and peripheral nerves; brain/spinal cord/peripheral nerve interfacing; wound healing; the treatment of infection (antibacterial/antiviral/antifungal); or enhancement of drug delivery/gene therapy following surgical resection.

In one embodiment there is provided a biphasic injectable electrode, as described herein, for use in the electrotherapy treatment of:
- brain tumors (including Grade I, II, III or IV glioma; pilocytic astrocytoma; subependymal giant cell astrocytoma; diffuse astrocytoma; oligodendroglioma; oligodendroglioma NOS; anaplastic astrocytoma; anaplastic oligodendroglioma; anaplastic oligodendroglioma NOS; glioblastoma; giant-cell glioblastoma; glioblastoma multiforme; subependymal giant cell astrocytoma; pilomyxoid astrocytoma; pleomorphic xanthoastrocytoma; ganglioglioma; oligoastrocytoma; meningiomas (including grade I, II or III meningioma and other neoplasms related to the meninges (for example haemangiopericytoma)); pediatric brain tumors (including ependymoma, medulloblastoma, atypical teratoid/rhabdoid tumor (AT/RT); choroid plexus papilloma; choroid plexus carcinoma; intracranial teratoma; and embryonal tumors with multilayered rosettes (ETMR)), pineal region tumors (for example pineoblastoma), and pituitary region tumors (for example pituitary adenoma, craniopharyngioma, and chordoma);

metastases of any cancer origin (for example brain metastasis including those from lung cancer, breast cancer, genitourinary tract cancer, osteosarcoma and melanoma);

lung cancer (including mesothelioma, malignant pleural mesothelioma, non-small cell-lung cancer and small cell lung cancer)

pancreatic cancer (for example locally advanced pancreatic adenocarcinoma);

ovarian cancer (for example ovarian cancer resistant to chemotherapy);

liver cancer (for example advanced hepatocellular cancer);

breast cancer;

cervical cancer;

colorectal carcinoma;

gastric cancer (including gastric adenocarcinoma);

spinal nerve sheath tumors (including schwannoma, neurofibroma and ganglioneuroma);

malignant melanoma;

renal adenocarcinoma; and urinary transitional cell carcinoma;

following surgical resection.

In one embodiment there is provided a biphasic injectable electrode, as described herein, for use in the electrotherapy treatment of:

brain metastases; and diffuse midline glioma;

following surgical resection.

In one embodiment there is provided a biphasic injectable electrode, as described herein, for use in the electrotherapy treatment of solid tumors following surgical resection.

In one embodiment there is provided a biphasic injectable electrode, as described herein, for use in the electrotherapy treatment of a Grade I, II, III or IV glioma following surgical resection.

In one embodiment there is provided a biphasic injectable electrode, as described herein, for use in the electrotherapy treatment of a Grade I glioma following surgical resection.

In one embodiment there is provided a biphasic injectable electrode, as described herein, for use in the electrotherapy treatment of pilocytic astrocytoma following surgical resection.

In one embodiment there is provided a biphasic injectable electrode, as described herein, for use in the electrotherapy treatment of a Grade II glioma following surgical resection.

In one embodiment there is provided a biphasic injectable electrode, as described herein, for use in the electrotherapy treatment of diffuse astrocytoma or oligodendroglioma following surgical resection.

In one embodiment there is provided a biphasic injectable electrode, as described herein, for use in the electrotherapy treatment of a Grade III glioma following surgical resection.

In one embodiment there is provided a biphasic injectable electrode, as described herein, for use in the electrotherapy treatment of anaplastic astrocytoma or anaplastic oligodendroglioma following surgical resection.

In one embodiment there is provided a biphasic injectable electrode, as described herein, for use in the electrotherapy treatment of a Grade IV glioma following surgical resection.

In one embodiment there is provided a biphasic injectable electrode, as described herein, for use in the electrotherapy treatment of diffuse midline glioma following surgical resection.

In one embodiment there is provided a biphasic injectable electrode, as described herein, for use in the electrotherapy treatment of brain metastases following surgical resection.

In one embodiment there is provided a biphasic injectable electrode, as described herein, for use in the electrotherapy treatment of giant-cell glioblastoma or glioblastoma multiforme following surgical resection.

In one embodiment there is provided a biphasic injectable electrode, as described herein, for use in the electrotherapy treatment of glioblastoma multiforme following surgical resection.

As used herein, the terms "treatment" and "treat" refer to reversing, alleviating, delaying the onset of, or inhibiting the progress of a disease or disorder, or one or more symptoms thereof, as described herein. In some embodiments, treatment may be conducted after one or more symptoms have developed. In other embodiments, treatment may be conducted in the absence of symptoms. For example, treatment may be conducted to a susceptible individual prior to the onset of symptoms (e.g., in light of a history of symptoms and/or in light of genetic or other susceptibility factors). Treatment may also be continued after symptoms have resolved, for example to present or delay their recurrence. Treatment may also be conducted for recurrent disease, for example recurrent GBM, or transforming disease where a previously lower grade (e.g., Grade II) glioma becomes a higher grade (e.g., Grade III or IV), or to prevent transforming disease.

Methods of Treatment

In one embodiment there is provided a biphasic injectable electrode, as described herein, for use in a method of treatment of the human or animal body by therapy.

In one embodiment there is provided a method of electrotherapy in a warm-blooded animal, such as man, which comprises administering to said animal a biphasic injectable electrode, as described herein.

In one embodiment there is provided a method of treating solid tumors; deep brain stimulation; spinal cord stimulation; peripheral nerve stimulation; retinal implants for restoration of vision; regeneration of nervous tissue including brain, spinal cord and peripheral nerves; brain/spinal cord/peripheral nerve interfacing; wound healing; the treatment of infection (antibacterial/antiviral/antifungal); or enhancement of drug delivery/gene therapy in a warm-blooded animal, such as man, which comprises administering electrotherapy to said animal comprising a biphasic injectable electrode, as described herein.

In one embodiment there is provided a method of treating:

brain tumors (including Grade I, II, III or IV glioma; pilocytic astrocytoma; subependymal giant cell astrocytoma; diffuse astrocytoma; oligodendroglioma; oligodendroglioma NOS; anaplastic astrocytoma; anaplastic oligodendroglioma; anaplastic oligodendroglioma NOS; glioblastoma; giant-cell glioblastoma; glioblastoma multiforme; subependymal giant cell astrocytoma; pilomyxoid astrocytoma; pleomorphic xanthoastrocytoma; ganglioglioma; oligoastrocytoma; meningiomas (including grade I, II or III meningioma and other neoplasms related to the meninges (for example haemangiopericytoma)); pediatric brain tumors (including ependymoma, medulloblastoma, atypical teratoid/rhabdoid tumor (AT/RT); choroid plexus papilloma; choroid plexus carcinoma; intracranial teratoma; and embryonal tumors with multilayered rosettes (ETMR)), pineal region tumors (for example pineoblastoma), and pituitary region tumors (for example pituitary adenoma, craniopharyngioma, and chordoma);

metastases of any cancer origin (for example brain metastasis including those from lung cancer, breast cancer, genitourinary tract cancer, osteosarcoma and melanoma);

lung cancer (including mesothelioma, malignant pleural mesothelioma, non-small cell-lung cancer and small cell lung cancer)

pancreatic cancer (for example locally advanced pancreatic adenocarcinoma);

ovarian cancer (for example ovarian cancer resistant to chemotherapy);

liver cancer (for example advanced hepatocellular cancer);

breast cancer;

cervical cancer;

colorectal carcinoma;

gastric cancer (including gastric adenocarcinoma);

spinal nerve sheath tumors (including schwannoma, neurofibroma and ganglioneuroma);

malignant melanoma;

renal adenocarcinoma; and urinary transitional cell carcinoma.

in a warm-blooded animal, such as man, which comprises administering electrotherapy to said animal comprising a biphasic injectable electrode, as described herein.

In one embodiment there is provided a method of treating:
brain metastases; and
diffuse midline glioma;
in a warm-blooded animal, such as man, which comprises administering electrotherapy to said animal comprising a biphasic injectable electrode, as described herein.

In one embodiment there is provided a method of treating solid tumors in a warm-blooded animal, such as man, which comprises administering electrotherapy to said animal comprising a biphasic injectable electrode, as described herein.

In one embodiment there is provided a method of treating a Grade I, II, III or IV glioma in a warm-blooded animal, such as man, which comprises administering electrotherapy to said animal comprising a biphasic injectable electrode, as described herein.

In one embodiment there is provided a method of treating a Grade I glioma in a warm-blooded animal, such as man, which comprises administering electrotherapy to said animal comprising a biphasic injectable electrode, as described herein.

In one embodiment there is provided a method of treating pilocytic astrocytoma in a warm-blooded animal, such as man, which comprises administering electrotherapy to said animal comprising a biphasic injectable electrode, as described herein.

In one embodiment there is provided a method of treating a Grade II glioma in a warm-blooded animal, such as man, which comprises administering electrotherapy to said animal comprising a biphasic injectable electrode, as described herein.

In one embodiment there is provided a method of treating astrocytoma or oligodendroglioma in a warm-blooded animal, such as man, which comprises administering electrotherapy to said animal comprising a biphasic injectable electrode, as described herein.

In one embodiment there is provided a method of treating a Grade III glioma in a warm-blooded animal, such as man, which comprises administering electrotherapy to said animal comprising a biphasic injectable electrode, as described herein.

In one embodiment there is provided a method of treating anaplastic astrocytoma or anaplastic oligodendroglioma in a warm-blooded animal, such as man, which comprises administering electrotherapy to said animal comprising a biphasic injectable electrode, as described herein.

In one embodiment there is provided a method of treating a Grade IV glioma in a warm-blooded animal, such as man, which comprises administering electrotherapy to said animal comprising a biphasic injectable electrode, as described herein.

In one embodiment there is provided a method of treating diffuse midline glioma in a warm-blooded animal, such as man, which comprises administering electrotherapy to said animal comprising a biphasic injectable electrode, as described herein.

In one embodiment there is provided a method of treating brain metastases in a warm-blooded animal, such as man, which comprises administering electrotherapy to said animal comprising a biphasic injectable electrode, as described herein.

In one embodiment there is provided a method of treating giant-cell glioblastoma or glioblastoma multiforme in a warm-blooded animal, such as man, which comprises administering electrotherapy to said animal comprising a biphasic injectable electrode, as described herein.

In one embodiment there is provided a method of treating solid tumors; deep brain stimulation; spinal cord stimulation; peripheral nerve stimulation; retinal implants for restoration of vision; regeneration of nervous tissue including brain, spinal cord and peripheral nerves; brain/spinal cord/peripheral nerve interfacing; wound healing; the treatment of infection (antibacterial/antiviral/antifungal); or enhancement of drug delivery/gene therapy following surgical resection in a warm-blooded animal, such as man, which comprises administering electrotherapy to said animal comprising a biphasic injectable electrode, as described herein.

In one embodiment there is provided a method of treating glioblastoma multiforme in a warm-blooded animal, such as man, which comprises administering electrotherapy to said animal comprising a biphasic injectable electrode, as described herein.

In one embodiment there is provided a method of treating:
brain tumors (including Grade I, II, III or IV glioma; pilocytic astrocytoma; subependymal giant cell astrocytoma; diffuse astrocytoma; oligodendroglioma; oligodendroglioma NOS; anaplastic astrocytoma; anaplastic oligodendroglioma; anaplastic oligodendroglioma NOS; glioblastoma; giant-cell glioblastoma; glioblastoma multiforme; subependymal giant cell astrocytoma; pilomyxoid astrocytoma; pleomorphic xanthoastrocytoma; ganglioglioma; oligoastrocytoma; meningiomas (including grade I, II or III meningioma and other neoplasms related to the meninges (for example haemangiopericytoma)); pediatric brain tumors (including ependymoma, medulloblastoma, atypical teratoid/rhabdoid tumor (AT/RT); choroid plexus papilloma; choroid plexus carcinoma; intracranial teratoma; and embryonal tumors with multilayered rosettes (ETMR)), pineal region tumors (for example pineoblastoma), and pituitary region tumors (for example pituitary adenoma, craniopharyngioma, and chordoma);

metastases of any cancer origin (for example brain metastasis including those from lung cancer, breast cancer, genitourinary tract cancer, osteosarcoma and melanoma);

lung cancer (including mesothelioma, malignant pleural mesothelioma, non-small cell-lung cancer and small cell lung cancer)

pancreatic cancer (for example locally advanced pancreatic adenocarcinoma);

ovarian cancer (for example ovarian cancer resistant to chemotherapy);

liver cancer (for example advanced hepatocellular cancer);

breast cancer;

cervical cancer;

colorectal carcinoma;

gastric cancer (including gastric adenocarcinoma);

spinal nerve sheath tumors (including schwannoma, neurofibroma and ganglioneuroma);

malignant melanoma;

renal adenocarcinoma; and urinary transitional cell carcinoma.

following surgical resection in a warm-blooded animal, such as man, which comprises administering electrotherapy to said animal comprising a biphasic injectable electrode, as described herein.

In one embodiment there is provided a method of treating:

brain metastases; and diffuse midline glioma;

following surgical resection in a warm-blooded animal, such as man, which comprises administering electrotherapy to said animal comprising a biphasic injectable electrode, as described herein.

In one embodiment there is provided a method of treating solid tumors following surgical resection in a warm-blooded animal, such as man, which comprises administering electrotherapy to said animal comprising a biphasic injectable electrode, as described herein.

In one embodiment there is provided a method of treating a Grade I, II, III or IV glioma following surgical resection in a warm-blooded animal, such as man, which comprises administering electrotherapy to said animal comprising a biphasic injectable electrode, as described herein.

In one embodiment there is provided a method of treating a Grade I glioma following surgical resection in a warm-blooded animal, such as man, which comprises administering electrotherapy to said animal comprising a biphasic injectable electrode, as described herein.

In one embodiment there is provided a method of treating pilocytic astrocytoma following surgical resection in a warm-blooded animal, such as man, which comprises administering electrotherapy to said animal comprising a biphasic injectable electrode, as described herein.

In one embodiment there is provided a method of treating a Grade II glioma following surgical resection in a warm-blooded animal, such as man, which comprises administering electrotherapy to said animal comprising a biphasic injectable electrode, as described herein.

In one embodiment there is provided a method of treating diffuse astrocytoma or oligodendroglioma following surgical resection in a warm-blooded animal, such as man, which comprises administering electrotherapy to said animal comprising a biphasic injectable electrode, as described herein.

In one embodiment there is provided a method of treating a Grade III glioma following surgical resection in a warm-blooded animal, such as man, which comprises administering electrotherapy to said animal comprising a biphasic injectable electrode, as described herein.

In one embodiment there is provided a method of treating anaplastic astrocytoma or anaplastic oligodendroglioma following surgical resection in a warm-blooded animal, such as man, which comprises administering electrotherapy to said animal comprising a biphasic injectable electrode, as described herein.

In one embodiment there is provided a method of treating a Grade IV glioma following surgical resection in a warm-blooded animal, such as man, which comprises administering electrotherapy to said animal comprising a biphasic injectable electrode, as described herein.

In one embodiment there is provided a method of treating diffuse midline glioma following surgical resection in a warm-blooded animal, such as man, which comprises administering electrotherapy to said animal comprising a biphasic injectable electrode, as described herein.

In one embodiment there is provided a method of treating brain metastases following surgical resection in a warm-blooded animal, such as man, which comprises administering electrotherapy to said animal comprising a biphasic injectable electrode, as described herein.

In one embodiment there is provided a method of treating giant-cell glioblastoma or glioblastoma multiforme following surgical resection in a warm-blooded animal, such as man, which comprises administering electrotherapy to said animal comprising a biphasic injectable electrode, as described herein.

In one embodiment there is provided a method of treating glioblastoma multiforme following surgical resection in a warm-blooded animal, such as man, which comprises administering electrotherapy to said animal comprising a biphasic injectable electrode, as described herein.

Multi-Electrode Electrotherapy

In one embodiment there is provided a form of electrotherapy comprising multiple cooperating electrodes implanted in soft tissue. These cooperating electrodes pass current between them, either in one direction under direct current conditions, or in both directions under alternating current conditions. This is herein referred to as "multi-electrode electrotherapy".

By using multiple cooperating implanted electrodes, e.g., along the circumference or periphery of the tumor or tumor resection margins, it is possible to reduce the maximum distance between any point in 3D space within the tumor or resection margins and the nearest implanted electrode. As a result, the minimum electrical field strength within the total volume of the tumor or resection margins will be increased. This in turn will reduce the input voltage required and therefore energy demand to generate a clinically effective electrical field, with resultant benefits to the battery life and total size of a stimulating device. This in turn may enable the complete implantation of the charge delivery device, with resultant benefit to patient quality of life without impacting treatment efficacy.

In one embodiment, multi-electrode electrotherapy could be administered by implanting more than one electrode.

In one embodiment, multi-electrode electrotherapy could be administered by implanting and/or injecting more than one electrode.

In one embodiment multi-electrode electrotherapy comprises two electrodes. In one embodiment multi-electrode electrotherapy comprises three electrodes. In one embodiment multi-electrode electrotherapy comprises four electrodes. In one embodiment multi-electrode electrotherapy comprises five electrodes. In one embodiment multi-electrode electrotherapy comprises six electrodes. In one embodiment multi-electrode electrotherapy comprises at least two electrodes. In one embodiment multi-electrode electrotherapy comprises at least three electrodes. In one embodiment multi-electrode electrotherapy comprises at least four electrodes. In one embodiment multi-electrode electrotherapy comprises at least five electrodes. In one embodiment multi-electrode electrotherapy comprises at least six electrodes.

In one embodiment multi-electrode electrotherapy comprises electrodes comprising platinum, a platinum alloy, platinum wire, iridium oxide, a platinum-iridium alloy, carbon, graphene, a conductive polymer, a conductive composite and/or a biphasic injectable electrode as described herein.

In one embodiment multi-electrode electrotherapy comprises a biphasic injectable electrode as described herein and an electrode comprising platinum, a platinum alloy, platinum wire, iridium oxide, a platinum-iridium alloy, carbon, graphene, a conductive polymer and/or a conductive composite.

In one embodiment multi-electrode electrotherapy comprises electrodes comprising platinum.

In one embodiment multi-electrode electrotherapy comprises electrodes comprising a platinum alloy.

In one embodiment multi-electrode electrotherapy comprises electrodes comprising platinum wire.

In one embodiment multi-electrode electrotherapy comprises electrodes comprising iridium oxide.

In one embodiment multi-electrode electrotherapy comprises electrodes comprising a platinum-iridium alloy.

In one embodiment multi-electrode electrotherapy comprises electrodes comprising carbon.

In one embodiment multi-electrode electrotherapy comprises electrodes comprising graphene.

In one embodiment multi-electrode electrotherapy comprises electrodes comprising a conductive polymer.

In one embodiment multi-electrode electrotherapy comprises electrodes comprising a conductive composite.

In one embodiment multi-electrode electrotherapy comprises electrodes comprising a biphasic injectable electrode, as described herein.

In one embodiment multi-electrode electrotherapy comprises a biphasic injectable electrode, as described herein, and an electrode comprising platinum.

In one embodiment multi-electrode electrotherapy comprises a biphasic injectable electrode, as described herein, and an electrode comprising a platinum alloy.

In one embodiment multi-electrode electrotherapy comprises a biphasic injectable electrode, as described herein, and an electrode comprising platinum wire.

In one embodiment multi-electrode electrotherapy comprises a biphasic injectable electrode, as described herein, and an electrode comprising iridium oxide.

In one embodiment multi-electrode electrotherapy comprises a biphasic injectable electrode, as described herein, and an electrode comprising a platinum-iridium alloy.

In one embodiment multi-electrode electrotherapy comprises a biphasic injectable electrode, as described herein, and an electrode comprising carbon.

In one embodiment multi-electrode electrotherapy comprises a biphasic injectable electrode, as described herein, and an electrode comprising graphene.

In one embodiment multi-electrode electrotherapy comprises a biphasic injectable electrode, as described herein, and an electrode comprising a conductive polymer.

In one embodiment multi-electrode electrotherapy comprises a biphasic injectable electrode, as described herein, and an electrode comprising a conductive composite.

In one embodiment there is provided multi-electrode electrotherapy for the treatment of solid tumors; deep brain stimulation; spinal cord stimulation; peripheral nerve stimulation; retinal implants for restoration of vision; regeneration of nervous tissue including brain, spinal cord and peripheral nerves; brain/spinal cord/peripheral nerve interfacing; wound healing; the treatment of infection (antibacterial/antiviral/antifungal); or enhancement of drug delivery/gene therapy.

In one embodiment there is provided multi-electrode electrotherapy for the treatment of:

brain tumors (including Grade I, II, III or IV glioma; pilocytic astrocytoma; subependymal giant cell astrocytoma; diffuse astrocytoma; oligodendroglioma; oligodendroglioma NOS; anaplastic astrocytoma; anaplastic oligodendroglioma; anaplastic oligodendroglioma NOS; glioblastoma; giant-cell glioblastoma; glioblastoma multiforme; subependymal giant cell astrocytoma; pilomyxoid astrocytoma; pleomorphic xanthoastrocytoma; ganglioglioma; oligoastrocytoma; meningiomas (including grade I, II or III meningioma and other neoplasms related to the meninges (for example haemangiopericytoma)); pediatric brain tumors (including ependymoma, medulloblastoma, atypical teratoid/rhabdoid tumor (AT/RT); choroid plexus papilloma; choroid plexus carcinoma; intracranial teratoma; and embryonal tumors with multilayered rosettes (ETMR)), pineal region tumors (for example pineoblastoma), and pituitary region tumors (for example pituitary adenoma, craniopharyngioma, and chordoma);

metastases of any cancer origin (for example brain metastasis including those from lung cancer, breast cancer, genitourinary tract cancer, osteosarcoma and melanoma);

lung cancer (including mesothelioma, malignant pleural mesothelioma, non-small cell-lung cancer and small cell lung cancer)

pancreatic cancer (for example locally advanced pancreatic adenocarcinoma);

ovarian cancer (for example ovarian cancer resistant to chemotherapy);

liver cancer (for example advanced hepatocellular cancer);

breast cancer;

cervical cancer;

colorectal carcinoma;

gastric cancer (including gastric adenocarcinoma);

spinal nerve sheath tumors (including schwannoma, neurofibroma and ganglioneuroma);

malignant melanoma;

renal adenocarcinoma; and urinary transitional cell carcinoma.

In one embodiment there is provided multi-electrode electrotherapy for the treatment of:

brain metastases; and diffuse midline glioma.

In one embodiment there is provided multi-electrode electrotherapy for the treatment of solid tumors.

In one embodiment there is provided multi-electrode electrotherapy for the treatment of a Grade I, II, III or IV glioma.

In one embodiment there is provided multi-electrode electrotherapy for the treatment of a Grade I glioma.

In one embodiment there is provided multi-electrode electrotherapy for the treatment of pilocytic astrocytoma.

In one embodiment there is provided multi-electrode electrotherapy for the treatment of a Grade II glioma.

In one embodiment there is provided multi-electrode electrotherapy for the treatment of diffuse astrocytoma or oligodendroglioma.

In one embodiment there is provided multi-electrode electrotherapy for the treatment of a Grade III glioma.

In one embodiment there is provided multi-electrode electrotherapy for the treatment of anaplastic astrocytoma or anaplastic oligodendroglioma.

In one embodiment there is provided multi-electrode electrotherapy for the treatment of a Grade IV glioma.

In one embodiment there is provided multi-electrode electrotherapy for the treatment of diffuse midline glioma.

In one embodiment there is provided multi-electrode electrotherapy for the treatment of brain metastases.

In one embodiment there is provided multi-electrode electrotherapy for the treatment of giant-cell glioblastoma or glioblastoma multiforme.

In one embodiment there is provided multi-electrode electrotherapy for the treatment of glioblastoma multiforme.

In one embodiment there is provided a method of treating solid tumors; deep brain stimulation; spinal cord stimulation; peripheral nerve stimulation; retinal implants for restoration of vision; regeneration of nervous tissue including brain, spinal cord and peripheral nerves; brain/spinal cord/peripheral nerve interfacing; wound healing; the treatment of infection (antibacterial/antiviral/antifungal); or enhancement of drug delivery/gene therapy in a warm-blooded animal, such as man, which comprises administering multi-electrode electrotherapy.

In one embodiment there is provided a method of treating:
brain tumors (including Grade I, II, III or IV glioma; pilocytic astrocytoma; subependymal giant cell astrocytoma; diffuse astrocytoma; oligodendroglioma; oligodendroglioma NOS; anaplastic astrocytoma; anaplastic oligodendroglioma; anaplastic oligodendroglioma NOS; glioblastoma; giant-cell glioblastoma; glioblastoma multiforme; subependymal giant cell astrocytoma; pilomyxoid astrocytoma; pleomorphic xanthoastrocytoma; ganglioglioma; oligoastrocytoma; meningiomas (including grade I, II or III meningioma and other neoplasms related to the meninges (for example haemangiopericytoma)); pediatric brain tumors (including ependymoma, medulloblastoma, atypical teratoid/rhabdoid tumor (AT/RT); choroid plexus papilloma; choroid plexus carcinoma; intracranial teratoma; and embryonal tumors with multilayered rosettes (ETMR)), pineal region tumors (for example pineoblastoma), and pituitary region tumors (for example pituitary adenoma, craniopharyngioma, and chordoma);
metastases of any cancer origin (for example brain metastasis including those from lung cancer, breast cancer, genitourinary tract cancer, osteosarcoma and melanoma);
lung cancer (including mesothelioma, malignant pleural mesothelioma, non-small cell-lung cancer and small cell lung cancer)
pancreatic cancer (for example locally advanced pancreatic adenocarcinoma);
ovarian cancer (for example ovarian cancer resistant to chemotherapy);
liver cancer (for example advanced hepatocellular cancer);
breast cancer;
cervical cancer;
colorectal carcinoma;
gastric cancer (including gastric adenocarcinoma);
spinal nerve sheath tumors (including schwannoma, neurofibroma and ganglioneuroma);
malignant melanoma;
renal adenocarcinoma; and
urinary transitional cell carcinoma.
in a warm-blooded animal, such as man, which comprises administering multi-electrode electrotherapy.

In one embodiment there is provided a method of treating:
brain metastases; and
diffuse midline glioma;
in a warm-blooded animal, such as man, which comprises administering multi-electrode electrotherapy.

In one embodiment there is provided a method of treating solid tumors in a warm-blooded animal, such as man, which comprises administering multi-electrode electrotherapy.

In one embodiment there is provided a method of treating a Grade I, II, III or IV glioma in a warm-blooded animal, such as man, which comprises administering multi-electrode electrotherapy.

In one embodiment there is provided a method of treating a Grade I glioma in a warm-blooded animal, such as man, which comprises administering multi-electrode electrotherapy.

In one embodiment there is provided a method of treating pilocytic astrocytoma in a warm-blooded animal, such as man, which comprises administering multi-electrode electrotherapy.

In one embodiment there is provided a method of treating a Grade II glioma in a warm-blooded animal, such as man, which comprises administering multi-electrode electrotherapy.

In one embodiment there is provided a method of treating astrocytoma or oligodendroglioma in a warm-blooded animal, such as man, which comprises administering multi-electrode electrotherapy.

In one embodiment there is provided a method of treating a Grade III glioma in a warm-blooded animal, such as man, which comprises administering multi-electrode electrotherapy.

In one embodiment there is provided a method of treating anaplastic astrocytoma or anaplastic oligodendroglioma in a warm-blooded animal, such as man, which comprises administering multi-electrode electrotherapy.

In one embodiment there is provided a method of treating a Grade IV glioma in a warm-blooded animal, such as man, which comprises administering multi-electrode electrotherapy.

In one embodiment there is provided a method of treating diffuse midline glioma in a warm-blooded animal, such as man, which comprises administering multi-electrode electrotherapy.

In one embodiment there is provided a method of treating brain metastases in a warm-blooded animal, such as man, which comprises administering multi-electrode electrotherapy.

In one embodiment there is provided a method of treating giant-cell glioblastoma or glioblastoma multiforme in a warm-blooded animal, such as man, which comprises administering multi-electrode electrotherapy.

In one embodiment there is provided a method of treating glioblastoma multiforme in a warm-blooded animal, such as man, which comprises administering multi-electrode electrotherapy.

Combinations

In some embodiments the electrotherapy comprising the biphasic injectable electrode, as described herein, may be administered in combination with chemotherapy and/or radiotherapy.

In some embodiments the electrotherapy comprising the biphasic injectable electrode, as described herein, may be administered in combination with chemotherapy and radiotherapy.

In some embodiments the electrotherapy comprising the biphasic injectable electrode, as described herein, may be administered in combination with chemotherapy.

In some embodiments the electrotherapy comprising the biphasic injectable electrode, as described herein, may be administered in combination with radiotherapy.

Herein, where the term "combination" is used it is to be understood that this refers to simultaneous, separate or sequential administration. In one aspect of the present disclosure, "combination" refers to simultaneous administration. In another aspect of the present disclosure, "combination" refers to separate administration. In a further aspect of the present disclosure, "combination" refers to sequential administration. Where the administration is sequential or separate, the delay in administering the second component should not be such as to lose the beneficial effect of the combination.

Kits

In one embodiment there is provided a kit comprising:
a) a biphasic injectable electrode, as described herein;
b) a counter electrode;
c) a probe; and
d) a charge delivery device.

In one embodiment there is provided a kit comprising:
a) a biphasic injectable electrode, as described herein;
b) a probe; and
c) a charge delivery device.

In one embodiment there is provided a kit comprising:
a) a biphasic injectable electrode, as described herein;
b) a counter electrode; and
c) a charge delivery device.

In one embodiment there is provided a kit comprising:
a) a biphasic injectable electrode as described herein;
b) a counter electrode; and
c) a probe.

In one embodiment there is provided a kit comprising:
a) a biphasic injectable electrode as described herein; and
b) a probe.

In one embodiment there is provided a kit comprising:
a) a biphasic injectable electrode as described herein; and
b) a charge delivery device.

In one embodiment there is provided a kit comprising:
a) a biphasic injectable electrode as described herein; and
b) a counter electrode.

In one embodiment there is provided a kit comprising:
a) a biphasic injectable electrode as described herein; and
b) a charge delivery device.

In one embodiment there is provided a kit comprising:
a) a biphasic injectable electrode as described herein; and
b) a counter electrode.

In one embodiment there is provided a kit comprising:
a) a biphasic injectable electrode as described herein; and
b) a probe.

In one embodiment there is provided a kit comprising:
a) two or more electrodes;
b) a charge delivery device.

In one embodiment there is provided a kit comprising:
a) three or more electrodes;
b) a charge delivery device.

In one embodiment there is provided a kit comprising:
a) four or more electrodes;
b) a charge delivery device.

In one embodiment there is provided a kit comprising:
a) five or more electrodes;
b) a charge delivery device.

EXAMPLES

The materials and apparatus used in the following Examples were purchased from the following suppliers:

| Material/apparatus | Supplier |
| --- | --- |
| Poly(3,4-ethylenedioxythiophene)-poly(styrenesulfonate) (PEDOT:PSS) (3-4%) (Supplier 1) | Sigma Aldrich ® UK |
| PEDOT:PSS (1-1.3%) (Supplier 2) | Ossila Ltd UK |
| Polyethylene glycol (PEG) | Sigma Aldrich ® UK |
| Polyvinyl alcohol (PVA) | Sigma Aldrich ® UK |
| Xanthan gum (XTN) | FisherScientific, UK |
| Dimethyl sulfoxide (DMSO) | Sigma Aldrich ® UK |
| Laponite ® RD ms16 (LP) | Conservation Resources ® UK Ltd |
| (3-Glycidyloxypropyl)trimethoxysilane (GOPS) | Sigma Aldrich ® UK |
| Ethylene glycol (EG) | Sigma Aldrich ® UK |
| Dodecylbenzenesulfonic acid (DBSA) | Sigma Aldrich ® UK |
| Methocel ® A15 LV (Methylcellulose) | Sigma Aldrich ® UK |
| Methocel ® A4 m | Sigma Aldrich ® UK |
| Steam autoclave | Classic, Prestige Medical ® |
| Sylgard 184 (includes polydimethylsiloxane (PDMS) and curing agent). Curing agent consists of poly(dimethylsiloxane-co-methylhydrosiloxane), trimethylsilyl terminated and 2,4,6,8-tetramethyl-2,4,6,8-tetravinylcyclotetrasiloxane | Sigma Aldrich ® UK |
| Oven | FisherScientific, UK |
| Freeze Dryer, Epsilon 2-6D LSCplus | Martin Christ |
| Phosphate Buffered Saline PBS), 10X Powder | FisherScientific, UK |
| Dialysis tubing, 4 kDa molecular weight cut off | Sigma Aldrich ® UK |

The biphasic injectable electrode comprises of two parts: the solid particles and the transporter phase in which the solid particles are distributed in the transporter phase. Examples 1 and 2 discuss the manufacturing of the solid particles of the biphasic injectable electrode and Examples 3 and 4 discuss manufacturing of the transporter phase. Example 5 outlines the combining of both parts to manufacture the biphasic injectable electrode.

Example 1

Manufacture of PEDOT:PSS Solid Particles for the Biphasic Injectable Electrodes

1A) PEDOT:PSS solution was mixed in a glass vial for 5 hours at room temperature before the addition of DMSO. After mixing for a set time, the PEDOT:PSS/DMSO suspension was cast in cylindrical molds with diameters of either 127.76 mm or 5 mm. Samples were left overnight at room temperature or on a hot plate set at 60° C., before being placed in an oven set at 60° C. until solid constructs were formed. In some samples, EG, GOPS and DBSA were added as stabilizing agents.

To remove the excess DMSO, solid constructs were washed with distilled water, phosphate buffered saline (PBS) and series of ethanol concentrations (30, 50, 70 and 100%), and then were stored in PBS until use. To make the PEDOT:PSS beads the constructs were punched out using a spherical punch of the desired size. The bead size ranges between (but is not limited to) 0.1 m to 1.5 mm.

| | PEDOT:PSS | | Stabilizing agents | | | | Processing | |
|---|---|---|---|---|---|---|---|---|
| Sample no. | PEDOT (ml) | PEDOT supplier | EG (μl) | GOPS (μl) | DBSA (μl) | DMSO (ml) | Mixing after addition of DMSO | Mold diameter (mm) |
| 1A.1 | 2.5 | Sigma | 112 | 23.4 | 2.3 | 2.5 | 5 mins | 127.76 |
| 1A.2 | 2.5 | Sigma | 112 | 23.4 | 2.3 | 2.5 | 5 mins | 5 |
| 1A.3 | 2.5 | Sigma | 112 | 23.4 | 2.3 | 2.5 | 24 hrs | 127.76 |
| 1A.4 | 2.5 | Sigma | 112 | 23.4 | 2.3 | 2.5 | 24 hrs | 5 |
| 1A.5 | 2.5 | Sigma | 112 | 23.4 | — | 2.5 | 24 hrs | 5 |
| 1A.6 | 2.5 | Sigma | 112 | — | — | 2.5 | 24 hrs | 5 |
| 1A.7 | 2.5 | Sigma | — | — | — | 2.5 | 24 hrs | 127.76 |
| 1A.8 | 2.5 | Sigma | — | — | — | 2.5 | 24 hrs | 5 |
| 1A.9 | 2.5 | Sigma | 112 | 23.4 | 2.3 | 1.75 | 5 mins | 127.76 |
| 1A.10 | 2.5 | Sigma | 112 | 23.4 | 2.3 | 1.75 | 5 mins | 5 |
| 1A.11 | 2.5 | Sigma | 112 | 23.4 | 2.3 | 1.75 | 24 hrs | 127.76 |
| 1A.12 | 2.5 | Sigma | 112 | 23.4 | 2.3 | 1.75 | 24 hrs | 5 |
| 1A.13 | 2.5 | Sigma | 112 | 23.4 | 2.3 | 1.7 | 24 hrs | 127.76 |
| 1A.14 | 2.5 | Ossila | 112 | 23.4 | 2.3 | 2.5 | 24 hrs | 127.76 |
| 1A.15 | 2.5 | Ossila | 112 | 23.4 | — | 2.5 | 24 hrs | 127.76 |
| 1A.16 | 2.5 | Ossila | 112 | — | — | 2.5 | 24 hrs | 127.76 |
| 1A.17 | 2.5 | Ossila | 112 | 23.4 | — | 2.5 | 24 hrs | 5 |
| 1A.18 | 2.5 | Ossila | 112 | 23.4 | 2.3 | 1.7 | 24 hrs | 127.76 |
| 1A.19 | 2.5 | Ossila | 112 | 23.4 | — | 1.7 | 24 hrs | 127.76 |

1B) PEDOT:PSS alone or with additional stabilizing agents (EG, GOPS, DBSA) and/or PBS was used to make particles. A solution of PEDOT:PSS, optionally with the additional ingredients, was dropped into liquid nitrogen to form particles. Liquid nitrogen was removed, and the frozen particles were freeze dried overnight. To anneal, the particles were then placed in an oven set at 180° C. for 1 hour. Fully formed particles were submerged in PBS for 8-24 hrs and were stored in PBS until use.

The bead size range between (but is not limited to) 0.1 m to 3 mm and is dependent on the syringe/needle used and the flow rate of the solution.

| | PEDOT:PSS | | | Stabilizers | | |
|---|---|---|---|---|---|---|
| Sample no. | PEDOT (ml) | PEDOT supplier | PBS (ml) | EG (μl) | GOPS (μl) | DBSA (μl) |
| 1B.1 | 5 | Ossila | — | — | — | — |
| 1B.2 | 2.5 | Ossila | — | 112 | 23.4 | 2.3 |
| 1B.3 | 2.5 | Ossila | — | 112 | 23.4 | — |
| 1B.4 | 4 | Ossila | 1 | — | — | — |
| 1B.5 | 3.75 | Ossila | 0.25 | — | — | — |

Example 2

Manufacture of PEDOT:PSS Solid Particles for the Biphasic Injectable Electrodes with the Addition of Synthetic Polymers 2A) One or more polymers were added directly into a PEDOT:PSS solution and mixed for 1 hour at 60° C. followed by 4 hours at room temperature. In some samples EG, GOPS and DBSA were added as stabilizing agents. DMSO was then added into the PEDOT:PSS/polymer solution, followed by mixing for a set time. The solutions were cast into cylindrical molds (diameter=127.76 mm) and put into an oven set at 60° C. until the constructs were fully cured. Once fully cured, the solid constructs were left at room temperature for 24 hours. These constructs were then washed in distilled water, PBS and a series of ethanol dilutions (30, 50, 70 and 100%), to remove excess DMSO, and were stored in PBS until use (room temperature). Constructs were then punched using a spherical punch to obtain beads in the range of 0.1 to 1 mm in size.

|  | Polymer | | | | PEDOT:PSS | | Stabilizing agents | | | Processing | |
| --- | --- | --- | --- | --- | --- | --- | --- | --- | --- | --- | --- |
| Sample no. | PVA (mg) | PEG (mg) | XTN (mg) | LP (mg) | PEDOT (ml) | PEDOT supplier | EG (µl) | GOPS (µl) | DBSA (µl) | DMSO (ml) | Mixing after addtn of DMSO |
| 2A.1 | 100 | — | — | — | 2 | Ossila | 89.6 | 18.6 | — | 1.4 | 24 hrs |
| 2A.2 | 100 | 10 | — | — | 2 | Ossila | 89.6 | 18.6 | — | 1.4 | 24 hrs |
| 2A.3 | 100 | — | — | — | 2 | Ossila | 89.6 | 18.6 | — | 2 | 24 hrs |
| 2A.4 | 100 | — | — | — | 2 | Ossila | 179.2 | 37.2 | — | 1.4 | 24 hrs |
| 2A.5 | 250 | — | — | — | 5 | Ossila | 179.2 | 37.2 | — | 3.5 | 24 hrs |
| 2A.6 | 100 | — | 30 | — | 2 | Ossila | 89.6 | 18.6 | — | 1.4 | 24 hrs |
| 2A.7 | 50 | — | — | 30 | 1 | Ossila | 44.8 | 9.3 | — | 0.7 | 24 hrs |
| 2A.8 | 50 | 50 | 20 | 20 | 1 | Ossila | 44.8 | 9.3 | — | 0.7 | 24 hrs |
| 2A.9 | 50 | — | 20 | — | 1 | Ossila | 44.8 | 9.3 | — | 0.7 | 24 hrs |
| 2A.10 | 50 | 50 | — | — | 1 | Ossila | 44.8 | 9.3 | — | 1 | 24 hrs |
| 2A.11 | 50 | 100 | — | — | 1 | Ossila | 44.8 | 9.3 | — | 1 | 24 hrs |
| 2A.12 | 25 | 50 | — | — | 1 | Ossila | 44.8 | 9.3 | — | 1 | 24 hrs |
| 2A.13 | 25 | 25 | — | — | 1 | Ossila | 44.8 | 9.3 | — | 1 | 24 hrs |
| 2A.14 | — | 100 | — | — | 1 | Ossila | 44.8 | 9.3 | — | 0.7 | 24 hrs |
| 2A.15 | 50 | — | — | — | 1 | Ossila | 44.8 | 9.3 | — | 0.7 | 24 hrs |
| 2A.16 | 50 | 50 | — | — | 1 | Ossila | 44.8 | 9.3 | — | 0.7 | 24 hrs |
| 2A.17 | 50 | 100 | — | — | 1 | Ossila | 44.8 | 9.3 | — | 0.7 | 24 hrs |
| 2A.18 | 10 | 10 | — | — | 1 | Ossila | 44.8 | 9.3 | — | 1 | 24 hrs |
| 2A.19 | — | 50 | — | — | 2.5 | Sigma | 112 | 23.4 | 2.3 | 2.5 | 5 mins |
| 2A.20 | — | — | — | 50 | 2.5 | Sigma | 112 | 23.4 | 2.3 | 2.5 | 5 mins |
| 2A.21 | 50 | — | — | — | 1 | Sigma | 44.8 | 9.3 | — | 1 | 5 mins |
| 2A.22 | 100 | — | — | — | 1 | Sigma | 44.8 | 9.3 | — | 1 | 5 mins |
| 2A.23 | — | 50 | — | — | 1 | Sigma | 44.8 | 9.3 | — | 1 | 5 mins |
| 2A.24 | — | 50 | — | — | 1 | Sigma | 44.8 | 9.3 | — | 0.8 | 30 mins |
| 2A.25 | 50 | — | — | — | 1 | Sigma | 44.8 | 9.3 | — | 0.8 | 30 mins |
| 2A.26 | 100 | — | — | — | 1 | Sigma | 44.8 | 9.3 | — | 0.8 | 30 mins |
| 2A.27 | 50 | 50 | — | — | 1 | Sigma | 44.8 | 9.3 | — | 1 | 24 hrs |
| 2A.28 | 50 | 100 | — | — | 1 | Sigma | 44.8 | 9.3 | — | 1 | 24 hrs |
| 2A.29 | 25 | 50 | — | — | 1 | Sigma | 44.8 | 9.3 | — | 1 | 24 hrs |
| 2A.30 | 25 | 25 | — | — | 1 | Sigma | 44.8 | 9.3 | — | 1 | 24 hrs |
| 2A.31 | — | 100 | — | — | 1 | Sigma | 44.8 | 9.3 | — | 0.7 | 24 hrs |
| 2A.32 | 50 | — | — | — | 1 | Sigma | 44.8 | 9.3 | — | 0.7 | 24 hrs |
| 2A.33 | 50 | 50 | — | — | 1 | Sigma | 44.8 | 9.3 | — | 0.7 | 24 hrs |
| 2A.34 | 50 | 100 | — | — | 1 | Sigma | 44.8 | 9.3 | — | 0.7 | 24 hrs |
| 2A.35 | 10 | 10 | — | — | 1 | Sigma | 44.8 | 9.3 | — | 1 | 24 hrs |

2B) One or more polymers were added directly into a PEDOT:PSS solution and mixed for 1 hour at 60° C. followed by 4 hours at room temperature. In some samples EG, GOPS and DBSA were added as stabilizing agents. This solution was then dropped into liquid nitrogen to form particles. Liquid nitrogen was removed and these frozen particles were then freeze dried overnight. The particles were then placed in an oven set at 180° C. for 1 hour to anneal. Samples were submerged in PBS for 8-24 hours and stored in PBS until use.

The bead size ranges between (but is not limited to) 0.1 m to 4 mm and is dependent on the syringe/needle used and the flow rate of the solution.

|  | PEDOT:PSS | | | Polymer | | Stabilizers | | |
| --- | --- | --- | --- | --- | --- | --- | --- | --- |
| Sample no. | PEDOT (ml) | PEDOT supplier | PBS (ml) | PVA (mg) | MC (g) from 10% stock | EG (µl) | GOPS (µl) | DBSA (µl) |
| 2B.1 | 5 | Ossila | — | 250 | — | — | — | — |
| 2B.2 | 5 | Ossila | — | 250 | — | 112 | 23.4 | 2.3 |
| 2B.3 | 5 | Ossila | — | 250 | — | 112 | 23.4 | — |
| 2B.4 | 1.25 | Ossila | — | — | 3.75 | — | — | — |
| 2B.5 | 3.75 | Ossila | — | — | 1.25 | 112 | — | — |
| 2B.6 | 3.75 | Ossila | — | — | 1.25 | — | — | — |
| 2B.7 | 3.75 | Ossila | 0.25 | — | 1 | — | — | — |

Example 3

Manufacture of PEDOT:PSS Transporter Phase for the Biphasic Injectable Electrodes 3A) PEDOT:PSS solution was mixed for 5 hours at room temperature. In some samples EG, GOPS and DBSA were added as stabilizing agents. DMSO was added to the PEDOT:PSS solution and the solution was stirred for 24 hours at room temperature. The solution was transferring into an oven set at 60° C. and was periodically mixed until a gel like viscosity was achieved. The sample was left at room temperature for at least 24 hours.

Dialysis of the sample was then performed to remove the excess DMSO. Dialysis involves transferring the PEDOT:PSS/polymer/DMSO sample into dialysis tubing. The sample loaded tube was then placed in a beaker with 600 ml of distilled water for 24 hours, 600 ml of PBS for 24 hours, followed by a series of ethanol washes (30, 50, 70%, 600 mls each) for 1 hour each and then finally in 600 ml of PBS for 24 hours. The sample was then removed from the dialysis tubing and due to the infiltration of PBS the sample was less viscous.

|  | PEDOT:PSS | | Stabilizing agents | | | Processing | |
|---|---|---|---|---|---|---|---|
| Sample no. | PEDOT (ml) | PEDOT supplier | EG (μl) | GOPS (μl) | DBSA (μl) | DMSO (ml) | Mixing after addition of DMSO | Time in oven |
| 3A.1 | 2.5 | Sigma | 112 | 23.4 | 2.3 | 2.5 | 24 hrs | 10 hrs |
| 3A.2 | 2.5 | Sigma | 112 | 23.4 | 2.3 | 2.5 | 5 mins | 10 hrs |
| 3A.3 | 2 | Ossila | — | — | — | 2 | 24 hrs | 8 hrs |
| 3A.4 | 2 | Ossila | 89.6 | 18.6 | — | 2 | 24 hrs | 8 hrs |
| 3A.5 | 2 | Ossila | 89.6 | 18.6 | — | 2.4 | 24 hrs | 8 hrs |
| 3A.6 | 2 | Ossila | 89.6 | 18.6 | — | 1.4 | 24 hrs | 8 hrs |
| 3A.7 | 2 | Ossila | 89.6 | 18.6 | — | 1.2 | 24 hrs | 8 hrs |
| 3A.8 | 2 | Ossila | 89.6 | 18.6 | — | 0.8 | 24 hrs | 8 hrs |
| 3A.9 | 5 | Ossila | 224 | 46.5 | — | 3.5 | 24 hrs | 14 hrs |

3B) In a glass vial, PBS buffer (10×) was mixed vigorously with deionized water for 10 seconds. PEDOT:PSS solution was added and was immediately mixed vigorously for no more than 10 seconds. The vial containing the sample was sealed and was placed in an oven at 90° C. for a set time. Once removed from the oven the sample was allowed to cool at room temperature.

|  | PEDOT:PSS | | | Deionized | Processing | |
|---|---|---|---|---|---|---|
| Sample no | PEDOT volume (ml) | PEDOT Supplier | PBS vol (ml) | water vol (ml) | Time in oven | Time to cool |
| 3B.1 | 0.5 | Ossila | 0.1 | 0.4 | 2 hrs | 1 hr |
| 3B.2 | 0.7 | Ossila | 0.1 | 0.2 | — | 24 hrs |
| 3B.3 | 0.7 | Ossila | 0.1 | 0.2 | 2 hrs | 1 hr |
| 3B.4 | 0.25 | Ossila | 0.1 | 0.65 | 2 hrs | 1 hr |

Example 4

Manufacture of PEDOT:PSS Transporter Phase for the Biphasic Injectable Electrodes with the addition of synthetic polymers 4A) One or more polymer was dissolved in PEDOT:PSS solution while mixing at 60° C. for 1 hour, followed by 4 hours of mixing at room temperature. In some samples, stabilizing agents including EG and GOPS were added to the PEDOT:PSS/polymer solution. DMSO was added into the solution and the solution was then mixed for 24 hours at room temperature. The solution was then transferred into an oven set at 60° C. and was periodically mixed until a viscous mixture was formed. The sample was left at room temperature for at least 24 hours.

Excess DMSO was removed from the sample using dialysis, which involves loading the dialysis tubing with the sample and carrying out a series of 600 ml washes (24 hours in distilled water, 24 hours in PBS, a series of ethanol washes 1 hour each including 30, 50 and 70%, and 24 hours in PBS). The sample was then transferred from the dialysis tubing into a glass vial.

|  | Polymer | | | | PEDOT:PSS | | Stabilizing agents | | | | Processing |
|---|---|---|---|---|---|---|---|---|---|---|---|
| Sample no. | PVA (mg) | PEG (mg) | XTN (mg) | LP (mg) | PEDOT (ml) | PEDOT supplier | EG (μl) | GOPS (μl) | DBSA (μl) | DMSO (ml) | Time in oven |
| 4A.1 | 250 | — | — | — | 5 | Ossila | 179.2 | 37.2 | — | 3.5 | 14 hrs |
| 4A.2 | 500 | — | — | — | 10 | Ossila | 358.4 | 358.4 | — | 7 | 14 hrs |
| 4A.3 | 50 | — | — | — | 2 | Ossila | 89.6 | 18.6 | — | 2 | 8 hrs |
| 4A.4 | 100 | — | — | — | 2 | Ossila | 89.6 | 18.6 | — | 2 | 8 hrs |
| 4A.5 | 250 | — | — | — | 5 | Ossila | 224 | 46.5 | — | 3.5 | 14 hrs |
| 4A.6 | 50 | 50 | — | — | 2 | Ossila | 89.6 | 18.6 | — | 2 | 8 hrs |
| 4A.7 | 50 | — | 20 | — | 2 | Ossila | 89.6 | 18.6 | — | 2 | 8 hrs |
| 4A.8 | 50 | — | 20 | 20 | 2 | Ossila | 89.6 | 18.6 | — | 2 | 8 hrs |
| 4A.9 | — | 50 | — | 20 | 2 | Ossila | 89.6 | 18.6 | — | 2 | 8 hrs |
| 4A.10 | 250 | — | — | — | 5 | Ossila | 179.2 | 80 | — | 3.5 | 14 hrs |
| 4A.11 | — | 50 | — | — | 2.5 | Sigma | 112 | 23.4 | 2.3 | 2.5 | 10 hrs |
| 4A.12 | — | — | — | 50 | 2.5 | Sigma | 112 | 23.4 | 2.3 | 2.5 | 10 hrs |
| 4A.13 | 50 | — | — | — | 1 | Sigma | 44.8 | 9.3 | — | 1 | 10 hrs |
| 4A.14 | 50 | — | — | — | 2 | Sigma | 89.6 | 18.6 | — | 2 | 8 hrs |

4B) To prepare methylcellulose stocks, water was added to a glass vial, stirred and heated to 90° C. Methylcellulose was gradually added into the heated water and was stirred for 15 minutes after complete dispersion. The solution was allowed to cool to room temperature with continued stirring. The vial was then sealed and transferred into an ice bath for 1 hour. The vial containing the sample was then placed in a fridge (4° C.) for 24 h hours.

To make the transporter phase, methylcellulose stock was mixed with PBS at room temperature for 1 minute. PEDOT:PSS solution was added and stirred until fully mixed.

| | Methylcellulose stock | | | Gel preparation | | | | |
|---|---|---|---|---|---|---|---|---|
| | Stock | A15LV | A4 m | Methylcellulose | PEDOT:PSS | | | PBS |
| Sample no | conc (% wt/wt) | MC (g) | MC (g) | Water (g) | stock (g) | PEDOT (ml) | PEDOT supplier | Conc | Vol (ml) |
| 4B.1 | 10 | 6.52 | — | 58.85 | 22.53 | 4.46 | Ossila | 10x | 3.19 |
| 4B.2 | 10 | 6.52 | — | 58.85 | 7.50 | 1.50 | Ossila | 10x | 1.00 |
| 4B.3 | 10 | 6.52 | — | 58.85 | 6.50 | 2.50 | Ossila | 10x | 1.00 |
| 4B.4 | 10 | 6.52 | — | 58.85 | 6.50 | 2.50 | Ossila | 20x | 1.00 |
| 4B.5 | 10 | 6.52 | — | 58.85 | 6.52 | 1.50 | Ossila | 10x | 1.00 |
| 4B.6 | 13.3 | 6.66 | — | 43.36 | 7.50 | 1.50 | Ossila | 10x | 1.00 |
| 4B.7 | 10 | 3.751 | 1.2506 | 45.02 | 6.25 | 3.00 | Ossila | 10x | 1.00 |
| 4B.8 | 10 | 3.751 | 1.2506 | 45.02 | 6.02 | 3 | Ossila | 20x | 1.00 |
| 4B.9 | 10 | 3.751 | 1.2506 | 45.02 | 6.50 | 2.50 | Ossila | 10x | 1.00 |
| 4B.10 | 10 | 3.751 | 1.2506 | 45.02 | 6.51 | 2.50 | Ossila | 20x | 1.00 |
| 4B.11 | 3 | — | 1.5 | 48.50 | 7.51 | 1.50 | Ossila | 10x | 1.00 |

Example 5

Combining the Solid Particles and Transporter Phase to Manufacture the Biphasic Injectable Electrode 5A) Any of the above transporter phases in example 3A and 4A may be mixed with any of the above solid particles in example 1A and 2A to make the biphasic injectable electrode. Optionally, in order to optimize the mechanical properties, one or more polymers may be mixed into the transporter phase and heated in an oven set at 120° C. for 20 minutes prior to the solid particles being added. The solid particles are then added into this mixture.

| | | | Polymer | | |
|---|---|---|---|---|---|
| | | | PDMS | | |
| Sample no. | Transporter phase | PVA (mg) | PDMS (µl) | Curing agent (µl) | Solid particles |
| 5A.1 | 1 ml of Sample 4A.1 | — | — | — | 2 ml of Sample 2A.5 |
| 5A.2 | 1 ml of Sample 4A.1 | — | — | — | 3 ml of Sample 2A.5 |
| 5A.3 | 1 ml of Sample 4A.1 | 80 | 20 | 30 | 2 ml of Sample 2A.5 |
| 5A.4 | 1 ml of Sample 4A.1 | — | 20 | 30 | 2 ml of Sample 2A.5 |
| 5A.5 | 1 ml of Sample 4A.1 | — | 40 | 30 | 2 ml of Sample 2A.5 |
| 5A.6 | 1 ml of Sample 4A.1 | 80 | 20 | 30 | 3 ml of Sample 2A.5 |

5B) Any of the above transporter phases in example 3B and 4B may be mixed with any of the above solid particles in example 1B and 2B to make the biphasic injectable electrode.

In some instances, any above transporter phase in all examples may be mixed with any of the above solid particles in all examples to make the biphasic gel electrode.

| Sample no. | Transporter phase | Solid particles |
|---|---|---|
| 5B.1 | 1 ml of sample 3B.2 | 0.0105 g of sample 2B.1 |
| 5B.2 | 1 ml of sample 3B.2 | 0.0157 g of sample 2B.1 |
| 5B.3 | 1 ml of sample 3B.2 | 0.021 g of sample 2B.1 |
| 5B.4 | 1 ml of sample 3B.2 | 0.0315 g of sample 2B.1 |
| 5B.5 | 1 ml of sample 3B.2 | 0.042 g of sample 2B.1 |
| 5B.6 | 1 ml of sample 4B.2 | 0.0105 g of sample 2B.1 |
| 5B.7 | 1 ml of sample 4B.2 | 0.0157 g of sample 2B.1 |
| 5B.8 | 1 ml of sample 4B.2 | 0.021 g of sample 2B.1 |
| 5B.9 | 1 ml of sample 4B.2 | 0.0315 g of sample 2B.1 |
| 5B.10 | 1 ml of sample 4B.2 | 0.042 g of sample 2B.1 |

Results
Experiment 1
Sample Capacitance and Charge Injection Properties

Figure 2:
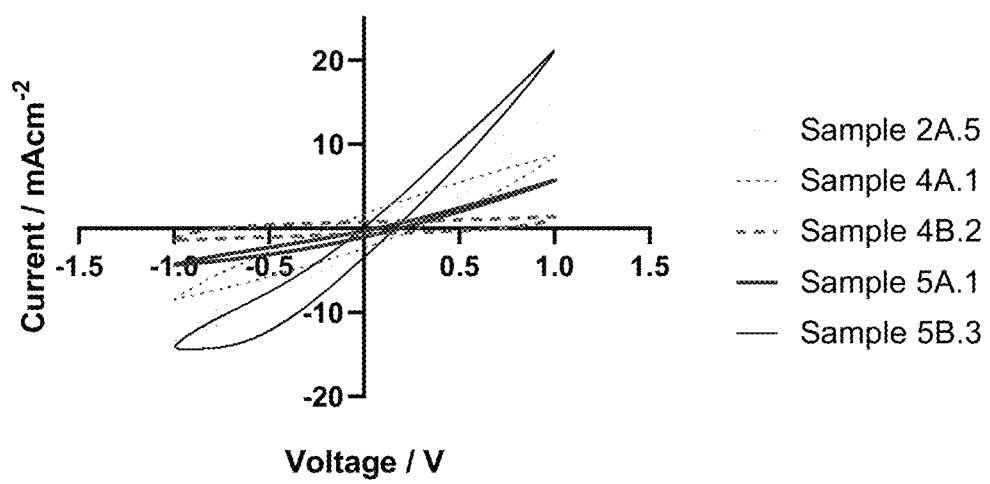
FIG. 2 shows the results from Experiment 1: Sample capacitance and charge injection properties. Potentials were applied between +1 and −1 V and the results at scan speed of 500 mVs$^{-1}$. In all instances these cyclic voltammograms indicate capacitive charge injection with smooth curves, and an absence of Faradaic peaks. The capacitive potential window of ±1V is the maximum potential that it is possible to apply without inducing electrolysis of water, and all samples were able to operate under a capacitive charge transfer regime in this environment in this potential window.
Figure 3:
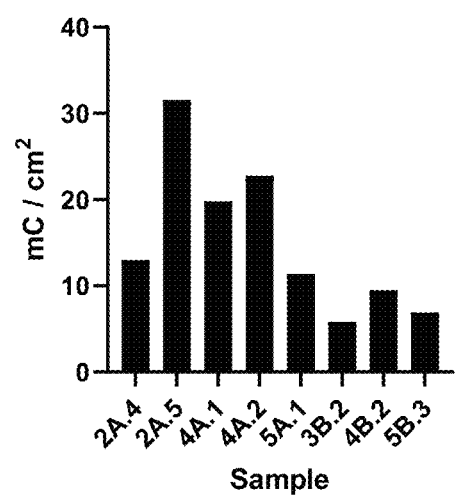
FIG. 3 shows the results from Experiment 1: Sample cathodal charge storage capacity (CSC). The results at scan speed of 500 mVs$^{-1}$ is shown. The CSC data for several different samples is shown. Charge storage capacity was calculated from cyclic voltammetry results. CSC results in this experiment exceeds current clinically used designs (SF Cogan; Neural Stimulation and recording electrodes; Annual Review of Biomedical Engineering; 2008) meaning all samples were capable of delivering more charge per voltage input compared to the current clinically used designs.
Figure 5:
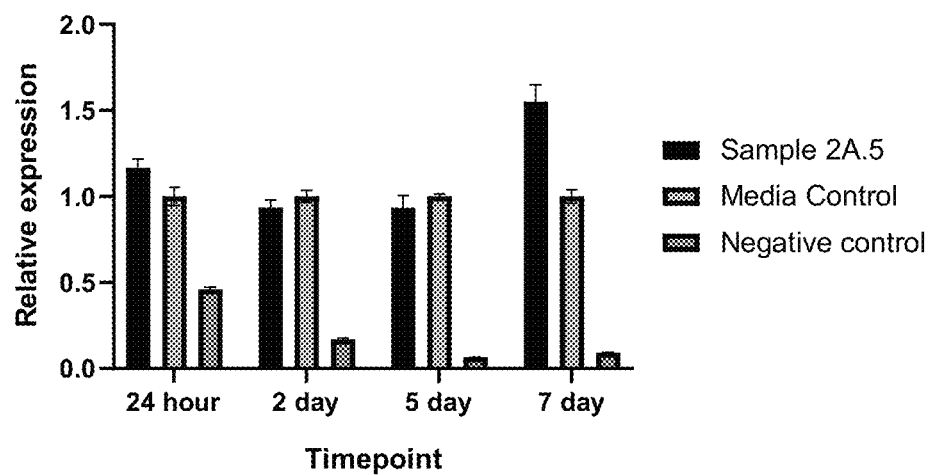
FIGS. 5 and 6 shows the results from Experiment 3: Sample biocompatibility with U251 human astrocyte like cells shown through detection of cell viability. Positive control consists of healthy cells grown in the well plate without the addition of samples. Negative control consists of cells grown in culture well plates without the addition of samples, but the cells are exposed to 5% dimethyl sulfoxide in the culture medium and this is known to have cytotoxic effects on these cells. Cell viability was similar in the sample and positive control demonstrating the biocompatibility of the sample.

Charge injection mechanisms were characterized by three-electrode cyclic voltammetry using a Bio-Logic Instruments, France, SP200 Potentiostat. The arrangement of the apparatus is shown in FIG. 5. 0.4 g of the sample acts as the working electrode. The electrolyte is 137 mM NaCl phosphate-buffered saline. The counter-electrode is an A-002222 platinum counter electrode (Biologic instruments, France) with outside diameter 0.5 mm and length 5 cm. This is inserted into the electrolyte to a depth of 0.5 mm, such that the distance between the counter-electrode and the sample is 0.5 mm. Measurements are made by a non-current-bearing reference electrode, which is an RE-1B Ag/AgCl reference electrode (Biologic instruments, France) with outside diameter 6 mm and length 80 mm. This is inserted into the electrolyte to a depth of 0.5 mm such that there is a distance of 0.5 mm between it and the sample. The reference electrode is physically distant to the counter-electrode. The sample was used as the working electrode, a A-002222 platinum counter electrode (Biologic instruments, France) with outside diameter 0.5 mm and length 5 cm was used. Potentials were applied between +1 and −1 V at scan rate of 500 mVs$^{-1}$. In all instances the working electrode (sample) area was 0.169 cm$^2$. The cyclic voltammetry results at scan speed of 500 mVs$^{-1}$ is shown in FIG. 2. The cathodal charge storage capacity was calculated from these results and is demonstrated in FIG. 3.

Experiment 2
Mechanical Properties

Storage moduli of samples was measured using the 'HR-2 Discovery rheometer' (TA instruments). The parallel plate geometry used was 20 mm with a gap of 500 μm 3 amplitude sweep tests were conducted per sample with a set soak time of 180 s, a temperature of 37° C. and a frequency of 1.0 Hz. Testing ceased when oscillation strain reached 20% (from the initial 0.01%). Value of G' is taken from the linear viscoelastic region and corresponds with the data point at 0.1% strain.

Figure 4:
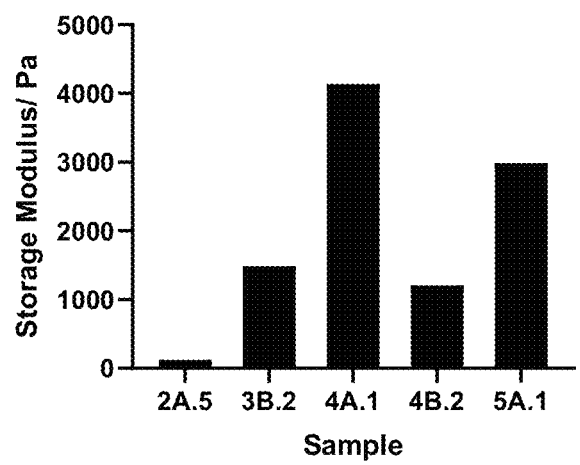
FIG. 4 shows the results from Experiment 2: Mechanical Properties. The mechanical properties of the samples were measured through oscillatory rheometry. The results indicate that the samples are very soft, with storage moduli in the low KPa range. Several samples fall within the stiffness range of the brain tissue itself (0.5-2 KPa) and all of the samples measured were many orders of magnitude softer (less stiff) than current clinical electrode materials (typically in the range of 100's of GPa) (e.g., Kostarelos et al.; Graphene in the design and engineering of next generation neural interfaces; Advanced Materials; 2017. https://doi.org/10.1002/adma.201700909).

The data indicate that the samples are very soft, with storage moduli in the low KPa range. Several samples fall within the stiffness range of the brain tissue itself (0.5-2 KPa). All of the samples measured were many orders of magnitude softer (less stiff) than current clinical electrode materials (typically in the range of 100's of GPa). The results are shown in FIG. 4.

Experiment 3
Sample Biocompatibility

Figure 6:
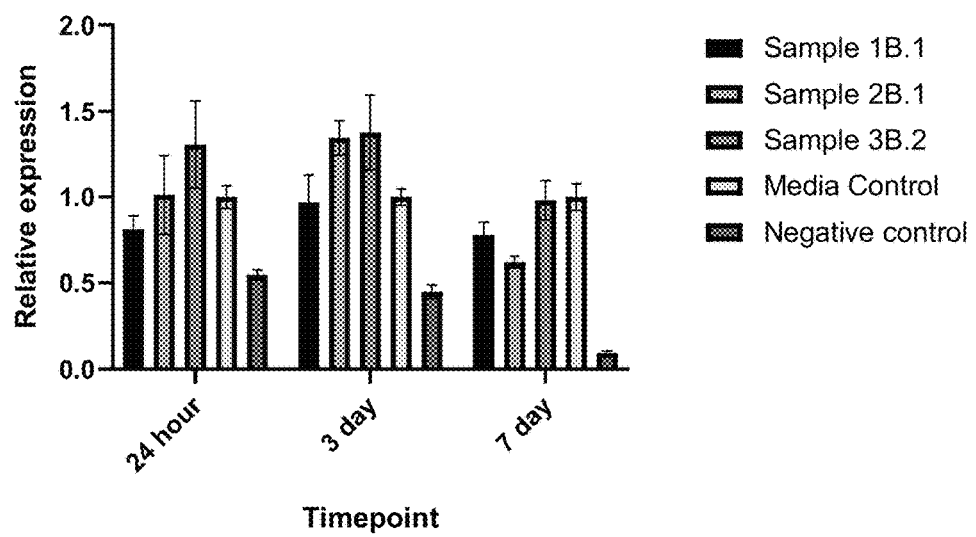
Figure 7:
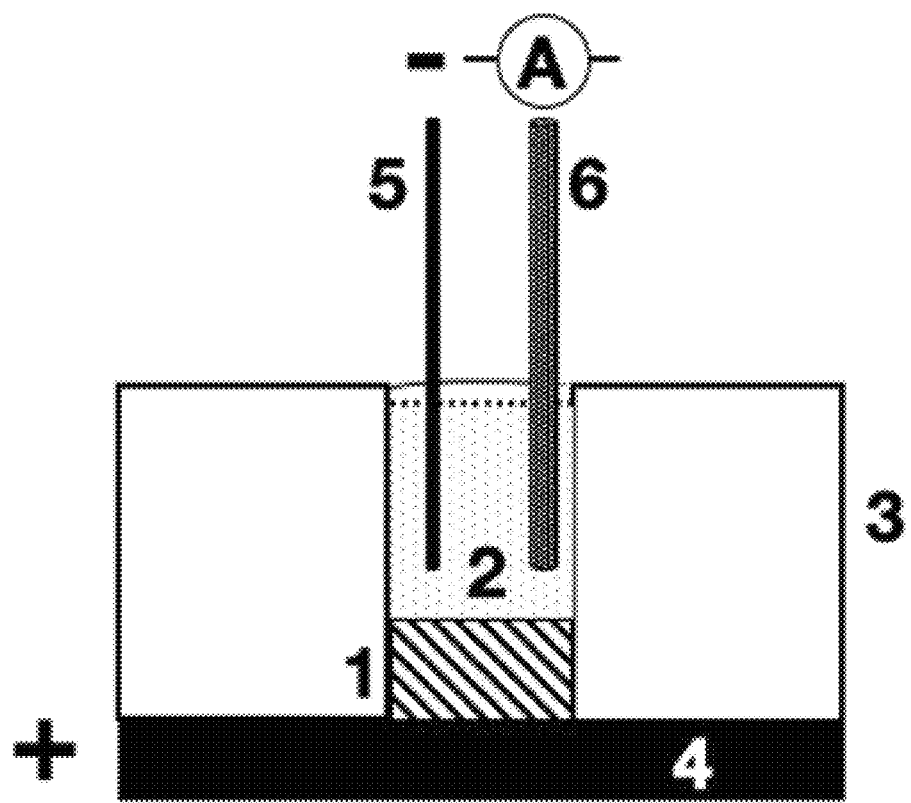
FIG. 7 shows a schematic of the testing cell used to perform the three-electrode cyclic voltammetry in experiment 1. The biphasic injectable electrode sample to be tested (1) sits within a well within a sample holder (3) created for the purpose from a solid block of polytetrafluorethylene. The sample (1) acts as the working electrode and is connected to a potentiostat via an electrically-conductive base (4) formed from a graphite composite. The electrolyte (2) is pipetted on top of the sample to submerge it. The counter-electrode (5) is inserted into the electrolyte. Measurements are made by a non-current-bearing reference electrode (6).

U251 human astrocyte-like cells were seeded directly into 24 well plates (Corning, UK) using standard culture conditions (Modified Eagle's Medium supplemented by 10% Foetal Bovine Serum and 100 units/mL Penicillin-Streptomycin, all supplied by Gibco, UK). For results in FIG. 5, seeding density of 20,000 cells per well was used. Cells were allowed 3 hours to adhere prior to placing two 0.7 mm×0.1 mm discs of Sample 2A.5 in each well. For FIG. 6, seeding density of 50,000 cells per well was used and cells were allowed 24 hours to adhere. Five 3 mm diameter particles (Sample 1B.1 and Sample 2B.1) were added to the appropriate wells and 1 ml of Sample 3B.2 was added to the appropriate wells. Samples were compared to a positive control for cell health, consisting of cells grown in the well plate in the absence of sample discs, this can be considered an ideal environment for cell culture. A negative control was also utilized, whereby cells were again grown in the well plate in the absence of the electrode sample but the media was further supplemented with 5% dimethyl sulfoxide, a compound with known cytotoxic activity at this concentration. Cell viability was measured using a resazurin reduction assay (Alamar Blue™, Thermofisher Scientific, UK), which was performed according to manufacturer's instructions. For FIG. 5, four separate experiments were undertaken with the data recorded at 24 hours, 3, 5 and 7 days of culture. For FIG. 6, three separate experiments were undertaken with the data recorded at 24 hours, 3, and 7 days of culture. The results are shown in FIGS. 5 and 6.

To better illustrate the systems and methods disclosed herein, a non-limiting list of examples of the subject matter disclosed herein (referred to as "STATEMENTS") are provided here:

Statement 1: A biphasic injectable electrode which comprises a plurality of solid particles and a transporter phase, wherein both the solid particles and the transporter phase comprise poly(3,4-ethylenedioxythiophene)polystyrene sulfonate.

Statement 2: A biphasic injectable electrode as stated in Statement 1, wherein the solid particles have a maximum dimension of 1.5 mm.

Statement 3: A biphasic injectable electrode as stated in either Statement 1 or Statement 2, wherein the solid particles consist of a gel.

Statement 4: A biphasic injectable electrode as stated in any one of Statements 1-3, wherein the solid particles comprise at least 90% v/v poly(3,4-ethylenedioxythiophene) polystyrene sulfonate.

Statement 5: A biphasic injectable electrode as stated in any one of Statements 1-4, wherein the solid particles comprise 60-85% v/v of the biphasic injectable electrode.

Statement 6: A biphasic injectable electrode as stated in any one of Statements 1-5, wherein the transporter phase consists of a shear thinning gel.

Statement 7: A biphasic injectable electrode as stated in any one of Statements 1-6, which comprises clay, polyethylene glycol, polyvinyl alcohol, polydimethylsiloxane, xanthan gum, (3-glycidyloxypropyl)trimethoxysilane, ethylene glycol, dodecylbenzenesulfonic acid, cyclodextrin and/or polyvinylamine.

Statement 8: A biphasic injectable electrode as stated in any one of Statements 1-7, which comprises polyvinyl alcohol, (3-glycidyloxypropyl)trimethoxysilane and/or ethylene glycol.

Statement 9: A biphasic injectable electrode as stated in any one of Statements 1-8, wherein the storage modulus of the biphasic injectable electrode is <2 kPa at an oscillation strain of 0.1% when assessed by oscillatory rheometry at a temperature of 37° C. and a frequency of 1 Hz.

Statement 10: A biphasic injectable electrode as stated in any one of Statements 1-9, wherein the biphasic injectable electrode is capable of delivering ±1V to human tissues under a capacitive charge transfer regime without inducing any Faradaic reactions.

Statement 11: An apparatus for use in electrotherapy, comprising a biphasic injectable electrode as stated in any one of Statements 1-10, a counter electrode, a probe, and a charge delivery device.

Statement 12: A biphasic injectable electrode as stated in any one of Statements 1-10 for use in electrotherapy.

Statement 13: A biphasic injectable electrode as stated in any one of Statements 1-10 for use in the electrotherapy treatment of solid tumors following surgical resection.

Statement 14: A method of treating glioblastoma multiforme following surgical resection in a warm-blooded animal, such as man, which comprises administering electrotherapy to said animal comprising a biphasic injectable electrode as stated in any one of Statements 1-10.

Statement 15: The use as stated in any one of Statements 12-14, or the method as stated in Statement 15, wherein treatment is administered in combination with chemotherapy and/or radiotherapy.

Statement 16: A kit comprising:
  a) a biphasic injectable electrode as stated in any one of Statements 1-10;
  b) a counter electrode;
  c) a probe; and
  d) a charge delivery device.

Statement 17: A method of electrotherapy comprising multiple cooperating electrodes implanted in soft tissue.

Statement 18: A method of electrotherapy as stated in Statement 17, which comprises at least four electrodes.

Statement 19: A method of electrotherapy as stated in either Statement 17 or Statement 18, which comprises a biphasic injectable electrode as stated in any one of Statements 1-10, and an electrode comprising platinum, a platinum alloy, platinum wire, iridium oxide, a platinum-iridium alloy, carbon, graphene, a conductive polymer, and/or a conductive composite.

Statement 20: A method of electrotherapy as stated in any one of Statements 17-19 for the treatment of solid tumors; deep brain stimulation; spinal cord stimulation; peripheral nerve stimulation; retinal implants for restoration of vision; regeneration of nervous tissue including brain, spinal cord and peripheral nerves; brain/spinal cord/peripheral nerve interfacing; wound healing; the treatment of infection (antibacterial/antiviral/antifungal); or enhancement of drug delivery/gene therapy.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A biphasic injectable electrode comprising a plurality of solid particles and a transporter phase, wherein the transporter phase comprises poly(3,4-ethylenedioxythiophene)polystyrene sulfonate and the solid particles comprise poly(3,4-ethylenedioxythiophene)polystyrene sulfonate, and wherein the solid particles are distributed within the transporter phase.

2. A biphasic injectable electrode as recited in claim 1, wherein the solid particles have a maximum dimension of 4 mm.

3. A biphasic injectable electrode as recited in claim 1, wherein the solid particles consist of a gel.

4. A biphasic injectable electrode as recited in claim 1, wherein the solid particles comprise at least 90% v/v poly(3,4-ethylenedioxythiophene)polystyrene sulfonate.

5. A biphasic injectable electrode as recited in claim 1, wherein the solid particles comprise 40-85% v/v of the biphasic injectable electrode.

6. A biphasic injectable electrode as recited in claim 1, wherein the transporter phase consists of a shear thinning gel.

7. A biphasic injectable electrode as recited in claim 1, wherein the transporter phase further comprises clay, polyethylene glycol (PEG), poly(ethylene glycol) methacrylate, poly(ethylene glycol)diacrylate, polyvinyl alcohol (PVA), polydimethylsiloxane (PDMS), xanthan gum, (3-glycidyloxypropyl)trimethoxysilane, ethylene glycol, dodecylbenzenesulfonic acid, methylcellulose, hydroxymethylcellulose, guar gum, Pluronic F-127, poly(N-isopropylacrylamide) (PNIPAAM), kappa-carrageenan, cyclodextrin, phosphate-buffered saline (PBS) and/or polyvinylamine.

8. A biphasic injectable electrode as recited in claim 1, wherein the transporter phase further comprises methylcellulose.

9. A biphasic injectable electrode as recited in claim 1, wherein a storage modulus of the biphasic injectable electrode is <5 kPa at an oscillation strain of 0.1% when assessed by oscillatory rheometry at a temperature of 37° C. and a frequency of 1 Hz.

10. A biphasic injectable electrode as recited in claim 1, wherein the biphasic injectable electrode is capable of delivering ±1 V to human tissues under a capacitive charge transfer regime without inducing any Faradaic reactions.

11. A biphasic injectable electrode as recited in claim 1, wherein the transporter phase comprises a less dense molecular network of poly(3,4-ethylenedioxythiophene) polystyrene sulfonate relative to the solid particles, wherein the less dense molecular network of poly(3,4-ethylenedioxythiophene)polystyrene sulfonate in the transporter phase confers some electrical conductivity to the transporter phase, wherein the electrical conductivity of the transporter phase is less than a corresponding electrical conductivity for the solid particles.

12. An apparatus for use in electrotherapy, comprising a biphasic injectable electrode as recited in claim 1, a counter electrode, a probe, and a charge delivery device.

13. A method of treatment comprising administering electrotherapy to a patient with a biphasic injectable electrode as recited in claim 1.

14. A method of treating a solid tumor following surgical resection in a warm-blooded animal, the method comprising administering electrotherapy to the animal with a biphasic injectable electrode as recited in claim 1.

15. A method as recited in claim 14, wherein the solid tumor is a glioblastoma multiforme.

16. The method as recited in claim 14, wherein treatment is administered in combination with chemotherapy, radiotherapy, or both.

17. A kit comprising:
a) a biphasic injectable electrode as recited in claim 1;
b) a counter electrode;
c) a probe; and
d) a charge delivery device.

18. A method of treatment comprising administering electrotherapy to a patient with a plurality of cooperating electrodes comprising at least one of the biphasic injectable electrode as recited in claim 1, wherein the plurality of cooperating electrodes are implanted in a soft tissue.

19. A method of treatment as recited in claim 18, wherein the plurality of cooperating electrodes comprises at least four electrodes.

20. A method of treatment as recited in claim 18 wherein the plurality of cooperating electrodes comprises at least one additional electrode, wherein each of the at least one additional electrodes comprises at least one of: platinum, a platinum alloy, a platinum wire, iridium oxide, a platinum-iridium alloy, carbon, graphene, a conductive polymer, and a conductive composite.

21. A method of treatment as recited in claim 18, wherein the electrotherapy is for at least one of: treatment of a solid tumor; deep brain stimulation; spinal cord stimulation; peripheral nerve stimulation; a retinal implant for restoration of vision; regeneration of nervous tissue including brain, spinal cord, and peripheral nerves; brain/spinal cord/peripheral nerve interfacing; wound healing; treatment of infection; or enhancement of drug delivery or gene therapy.

* * * * *